US008609849B1

(12) United States Patent
Smith et al.

(10) Patent No.: US 8,609,849 B1
(45) Date of Patent: Dec. 17, 2013

(54) HYDROXYLATED SULFAMIDES EXHIBITING NEUROPROTECTIVE ACTION AND THEIR METHOD OF USE

(75) Inventors: Garry Robert Smith, Royersford, PA (US); Douglas E. Brenneman, North Wales, PA (US); Allen B. Reitz, Lansdale, PA (US); Yan Zhang, Fort Washington, PA (US); Yanming Du, Cheshire, CT (US)

(73) Assignees: Fox Chase Chemical Diversity Center, Inc., Doylestown, PA (US); Advanced Neural Dynamics, Inc., Doylestown, PA (US)

( * ) Notice: Subject to any disclaimer, the term of this patent is extended or adjusted under 35 U.S.C. 154(b) by 63 days.

(21) Appl. No.: 13/306,103

(22) Filed: Nov. 29, 2011

Related U.S. Application Data

(60) Provisional application No. 61/417,945, filed on Nov. 30, 2010.

(51) Int. Cl.
*C07D 211/52* (2006.01)
*C07C 307/06* (2006.01)
*A61K 31/451* (2006.01)
*A61K 31/18* (2006.01)

(52) U.S. Cl.
USPC .............. 546/217; 564/79; 514/379; 514/600

(58) Field of Classification Search
USPC ...................... 546/217; 564/79; 514/327, 600
See application file for complete search history.

(56) References Cited

U.S. PATENT DOCUMENTS

| | | | |
|---|---|---|---|
| 5,698,588 A | 12/1997 | Choi | |
| 5,854,283 A | 12/1998 | Choi | |
| 2001/0034365 A1 | 10/2001 | Choi | |
| 2003/0220369 A1* | 11/2003 | Forman et al. ................ | 514/312 |
| 2008/0085930 A1 | 4/2008 | Peterson | |
| 2008/0090903 A1 | 4/2008 | Pandey | |
| 2008/0103127 A1 | 5/2008 | Haas | |
| 2008/0103198 A1 | 5/2008 | Haas | |
| 2008/0103199 A1 | 5/2008 | Haas | |
| 2009/0111872 A1 | 4/2009 | Embrechts | |
| 2009/0247616 A1 | 10/2009 | Smith-Swintosky | |

FOREIGN PATENT DOCUMENTS

| | | |
|---|---|---|
| WO | WO-9726241 A1 | 7/1997 |
| WO | WO-0207822 A2 | 1/2002 |
| WO | WO-0214275 A2 | 2/2002 |
| WO | WO-02067921 A1 | 9/2002 |
| WO | WO-02067922 A1 | 9/2002 |
| WO | WO02067923 A1 | 9/2002 |
| WO | WO-02067925 A1 | 9/2002 |
| WO | WO-02067926 A1 | 9/2002 |
| WO | WO-02067927 A1 | 9/2002 |
| WO | WO-03053916 A1 | 7/2003 |
| WO | WO-2006007435 A1 | 1/2006 |
| WO | WO-2006033947 A2 | 3/2006 |
| WO | WO-2006044472 A1 | 4/2006 |
| WO | WO-2006078524 A1 | 7/2006 |
| WO | WO-2006127184 A1 | 11/2006 |
| WO | WO-2007008551 A2 | 1/2007 |
| WO | WO-2007008562 A2 | 1/2007 |
| WO | WO-2007018496 A1 | 2/2007 |
| WO | WO-2007075698 A2 | 7/2007 |
| WO | WO-2007095613 A2 | 8/2007 |
| WO | WO-2007101116 A2 | 9/2007 |
| WO | WO-2007137164 A2 | 11/2007 |
| WO | WO2007143822 A1 | 12/2007 |
| WO | WO-2008055022 A2 | 5/2008 |
| WO | WO-2008063284 A2 | 5/2008 |
| WO | WO2008142134 A1 | 11/2008 |
| WO | WO-2009021129 A1 | 2/2009 |
| WO | WO-2009050587 A1 | 4/2009 |
| WO | WO-2009089210 A1 | 7/2009 |
| WO | WO-2009089235 A1 | 7/2009 |
| WO | WO-2009120189 A1 | 10/2009 |
| WO | WO-2010015029 A1 | 2/2010 |

OTHER PUBLICATIONS

Ciaping Yao, Dennis R. Doose, Gerald Novak, Maeir Bialer, Epilepsia, Oct. 26, 2006, 47, 11,1822-1829, Blackwell Publishing, US.
Suchean Chien, Meir Bailer, Bhavna Solanki, Tim Verhaeghe, Dennis R Doose, Gerald Novak, Epilepsia, Oct. 26, 2006, 47, 11, 1830-1840, Blackwell Publishing, US.
Jennifer Francois, Any Boehrer, Astrid Nehlig, Epilepsia, Sep. 5, 2007, 49, 3, 393-399, Blackwell Publishing.
Heidi L Grabenstatter, F Edward Dudek, Epilepsia, May 20, 2008, 49, 10, 1787-1794, John Wiley & Sons, US.
Laxmikant S Deshpande, Nisha Nagarkatti, Julie M Ziobro, Sompong Sombati Robert J Delorenzo, Epilepsia, May 20, 2008, 49, 10, 1795-1802, John Wiley & Sons, US.
Michael R Sperling, Epilepsia, Oct. 27, 2009, 51, 3, 333-343, John Wiley & Sons, US.
Michael A Rogawski, Epilepsy Research, Apr. 18, 2006, 69, 273-294, Elsevier B.V., US.
Rene Levy, Isabelle Ragueneau-Majlessi, Bhavna Solanki, Peter Zannikos, Ciaping Yao, Gerald Novak, Epilepsy Research, Feb. 14, 2008, 79, 22-30, Elsevier B.V., US.
Laxmikant S Deshpande, Nisha Nagarkatti, Sompong Sombati, Robert J Delorenzo, Epilepsy Research, Mar. 18, 2008, 79, 158-165, Elsevier B.V., US.
Yi Liu, George J Yohrling, Yan Wang, Tasha L Hutchinson, Douglas E Brenneman, Christopher M Flores, Boyu Zhao, Epilepsy Research, Nov. 14, 2008, 83, 66-72, Elsevier B.V., US.
Peter Zannikos, Gerald Novak, Caiping Yao, Tom Verhaeghe, Monique A Franc, Bhavna Solanki, Meir Bialer, Epilepsia, May 11, 2009, 50, 8, 1850-1859, John Wiley & Sons, US.
Wenju Wu, Stephen J Mehrman, Yong Zhou, Sean X Pu, Lian Huang, Adam Fermier, Shyam Karki, Journal of Crystal Growth, Jun. 15, 2009, 311, 3435-3444, Elsevier B.V., US.

(Continued)

*Primary Examiner* — David K O Dell
(74) *Attorney, Agent, or Firm* — Caesar, Rivise, Bernstein, Cohen & Pokotilow, Ltd.

(57) ABSTRACT

Pharmaceutical compositions of the invention include hydroxylated sulfamide derivatives having a disease-modifying action in the treatment of diseases associated with excitotoxicity and accompanying oxidative stress that include epilepsy, Alzheimer's disease, and any neurodegenerative disease involving glutamate toxicity.

15 Claims, No Drawings

(56) References Cited

OTHER PUBLICATIONS

E Faught, G L Holmes, W E Rosenfeld, G Novak, W Neto, a Greenspan, J Schmitt, E Yuen, Neurology, Nov. 11, 2008, 71, 1586-1593, American Academy of Neurology Enterprises, US.

G S J Mannens, J Hendrick, C G M Janssen, Drug Metabolism and Disposition, Aug. 25, 2006, 35, 4, 554-565, The American Society for Pharmacology and Experimental Therapeutics, US.

B J Whalley, G J Stephens, A Constanti, British Journal of Pharmacology, Feb. 18, 2009, 156, 994-1008, John Wiley & Sons, UK.

Guang Ri Dong, Qing Ri Li, Seol Hee Woo, In Su Kim, Archives of Pharmacal Research, Nov. 21, 2008, 31, 11, 1393-1398, Pharmaceutical Society of Korea, KR.

Amir H Rezvani, David H Overstreet, Anil H Vaidya, Boyu Zhao, Alcoholism: Clinical and Experimental Research, Apr. 30, 2009, 33, 8, 1366-1373, John Wiley & Sons, US.

Bengzon et al., "Neuronal apoptosis after brief and prolonged seizures", Progress in Brain Research, vol. 135, pp. 111-119, 2002.

Cavus et al., "Decreased hippocampal volume on MRI is associated with increased extracellular glutamate in epilepsy patients", Epilepsia, vol. 49, No. 8, pp. 1358-1366 (2008).

Ferriero, "Protecting Neurons", Epilepsia, vol. 46, pp. 45-51 (2005).

Jarrett et al., "Mitochondrial DNA damage and impaired base excision repair during epileptogenesis", Neurobiol Dis., vol. 30, No. 1, pp. 130-138 (2008).

Petroski et al., "Selective labeling of embryonic neurons . . .", Journal of Neuroscience Methods, vol. 52, pp. 23-32 (1994).

Randall, et al., "Glutamate-induced Calcium Transient Triggers Delayed Calcium Overload . . .", The Journal of Neuroscience, vol. 12, No. 5, pp. 1882-1895 (1992).

Van Den Pol et al., "Glutamate Hyperexcitability and Seizure-Like Activity Throughout the Brain and Spinal Cord Upon . . .", Neuroscience, vol. 74, No. 3, pp. 653-674 (1996).

White, "Animal Models for Evaluating Antiepileptogenesis", Jasper's Basic Mechanisms of the Epilepsies, pp. 1-17, 2010.

Waldbaum et al., "Mitochondrial dysfunction and oxidative stress: a contributing link to acquired epilepsy?", J. Bioenerg Biomembr., vol. 42, No. 6, pp. 449-455 (2010).

Van Den Pol et al., "Neuropeptide Y-Mediated Long-Term Depression of Excitatory Activity in . . .", The Journal of Neuroscience, vol. 16, No. 18, pp. 5883-5895 (1996).

Sarafian, et al., "Synergistic cytotoxicity of 9-tetrahydrocannabinol and butylated hydroxyanisole", Toxicology Letters, vol. 133, pp. 171-179 (2002).

Henshall et al., "Activation of Bcl-2-Associated Death Protein and Counter-Response of Akt within . . .", The Journal of Neuroscience, vol. 22, No. 19, pp. 8458-8465 (2002).

Wu et al., "Mitochondrial DNA Mutation-Elicited Oxidative Stress . . ." Mol Neurobiol (2010) 41:256-266.

\* cited by examiner

HYDROXYLATED SULFAMIDES EXHIBITING NEUROPROTECTIVE ACTION AND THEIR METHOD OF USE

STATEMENT OF FEDERALLY FUNDED RESEARCH

The U.S. Government has a paid-up license in this invention and the right in limited circumstances to require the patent owner to license others on reasonable terms as provided for by the terms of grant number 5R43NS066537-02 awarded by the National Institute of Neurological Disorders And Stroke.

FIELD OF INVENTION

The present invention describes compounds and methods useful as neuroprotective agents, useful for the treatment of epilepsy and related conditions. The present invention further describes a novel chemotype useful for the treatment of neurodegenerative disease, epilepsy, and other diseases that involve the presence of excess glutamate.

BACKGROUND OF THE INVENTION

Epilepsy is a common chronic neurological condition that affects over 50 million people worldwide, including approximately three million Americans. Although effective anticonvulsant drugs have been available since the early 1900's, significant unmet medical needs remain. Current estimates indicate that 25% of people suffering from epilepsy receive no effective treatment for their seizures from today's available drugs. Of those that do, approximately 15% report inadequate treatment and another 20% have intractable seizures. Serious toxicities (Stevens Johnson syndrome, metabolic acidosis, aplastic anemia), reduced bone mineral density and osteoporosis, and teratogenicity are concerns with currently marketed antiepileptic drugs.

Frequently identified causes of epileptic seizures include stroke, injuries, poisoning (alcoholism), and systemic illnesses during pregnancy or brain injuries during childbirth. However, for 65-75% of children and 50% of adults with epilepsy, no identifiable cause can be found. There are 30 marketed antiepileptic drugs, but all possess unwanted CNS side effects. In addition, while therapeutic intervention is possible with marketed compounds, approximately 25% of patients develop refractory epilepsy. These cases are treated with a combination of therapies that are often ineffective.

The neurochemical rationale for treating epileptogenesis resides in our understanding of the multiple factors that contribute to neuronal cell death in this disease (Bengzon et al., 2002). These factors include genetic factors, glutamate-induced excitotoxicty, mitochondrial dysfunction, oxidative stress, growth factor loss and increases in cytokine concentration (Ferriero, 2005). Intense seizure activity produces large increases NMDA-mediated calcium influx (Van Den Pol et al., 1996). High levels of calcium lead to apoptotic cascades that result in acute neuronal cell death. Elevated calcium levels can also generate reactive oxygen species that can produce cell damage and death. In addition, neuronal injury and death have been shown to occur in most epilepsy models and are widely considered both a prerequisite and a result of seizure-induced epilepsy. Two of the processes that contribute to the neural losses are glutamate toxicity and oxidative stress. An emerging concept is that neuroprotection by prevention of glutamate toxicity and oxidative stress will limit both neural damage associated with seizures and provide long-term antiepileptogenesis. The same strategy has been suggested for the treatment of or preventing diseases with excess glutamate in their etiology, including, for example, Parkinson's disease, Alzheimer's, and Huntington's disease.

There is a long felt need for new antiepileptic drugs that are both disease-modifying and effective in treating patients that are refractory to current treatments. There is also a clear and present need for antiepileptic drugs with lower toxicity and higher therapeutic index. The present invention addresses the need to prevent glutamate toxicity and oxidative stress in addition to providing neurostabilization to treat acute seizures and epilepsy. The present invention also addresses the long felt need for new treatments for and means of preventing diseases with excess glutamate in their etiology, including, for example, epilepsy, Parkinson's disease, Alzheimer's, and Huntington's disease.

BRIEF SUMMARY OF THE INVENTION

The present invention is directed toward novel hydroxylated sulfamide derivatives, compounds of formula (I),

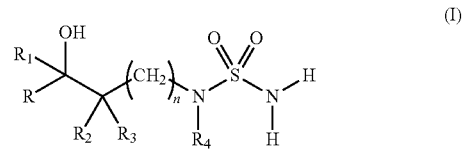

including hydrates, solvates, pharmaceutically acceptable salts, prodrugs and complexes thereof, wherein:

R is selected from the group consisting of optionally substituted aryl, optionally substituted benzoisoxazole, and optionally substituted benzothiophene where R may be substituted by 0-5 moieties;

n is 1 or 2;

$R^1$ is selected from the group consisting of hydrogen and optionally substituted $C_{1-6}$ alkyl;

$R^2$, $R^3$, and $R^4$ are each independently selected from the group consisting of hydrogen, halogen, and optionally substituted $C_{1-6}$ alkyl; and $R^1$ and $R^4$ are taken together with atoms to which they are bound to form an optionally substituted ring having from 5 to 7 ring atoms.

The present invention further relates to compositions comprising:

an effective amount of one or more compounds according to the present invention and an excipient.

The present invention also relates to a method for treating or preventing diseases that involve excess glutamate in their etiology, including, for example, epilepsy, Parkinson's disease, Alzheimer's, and Huntington's disease, said method comprising administering to a subject an effective amount of a compound or composition according to the present invention.

The present invention yet further relates to a method for treating or preventing diseases that involve excess glutamate in their etiology, including, for example, epilepsy, Parkinson's disease, Alzheimer's, and Huntington's disease, wherein said method comprises administering to a subject a composition comprising an effective amount of one or more compounds according to the present invention and an excipient.

The present invention also relates to a method for treating or preventing disease or conditions associated with epilepsy, Parkinson's disease, Alzheimer's, Huntington's disease, and diseases that involve excess glutamate in their etiology. Said methods comprise administering to a subject an effective amount of a compound or composition according to the present invention.

The present invention yet further relates to a method for treating or preventing disease or conditions associated with epilepsy, Parkinson's disease, Alzheimer's, Huntington's disease, and diseases that involve excess glutamate in their etiology, wherein said method comprises administering to a subject a composition comprising an effective amount of one or more compounds according to the present invention and an excipient.

The present invention also relates to a method for treating or preventing disease or conditions associated with neuronal cell death or damage from glutamate toxicity. Said methods comprise administering to a subject an effective amount of a compound or composition according to the present invention.

The present invention yet further relates to a method for treating or preventing disease or conditions associated with neuronal cell death or damage from glutamate toxicity, wherein said method comprises administering to a subject a composition comprising an effective amount of one or more compounds according to the present invention and an excipient.

The present invention also relates to a method for treating or preventing disease or conditions associated with neuronal cell death or damage from oxidative stress. Said methods comprise administering to a subject an effective amount of a compound or composition according to the present invention.

The present invention yet further relates to a method for treating or preventing disease or conditions associated with neuronal cell death or damage from oxidative stress, wherein said method comprises administering to a subject a composition comprising an effective amount of one or more compounds according to the present invention and an excipient.

The present invention further relates to a process for preparing the neuroprotective agents of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The neuroprotective agents of the present invention are capable of treating and preventing diseases associated with glutamate toxicity and oxidative stress including, for example epilepsy, Parkinson's disease, Alzheimer's disease, and Huntington's disease. It has been discovered that prevention of glutamate toxicity and oxidative stress will limit neural damage associated with seizures, provide long-term antiepileptogenesis, and prevent neuronal cell death. Without wishing to be limited by theory, it is believed that neuroprotective agents can ameliorate, abate, otherwise cause to be controlled, diseases associated with glutamate toxicity, oxidative stress, and neuronal cell death.

Throughout the description, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_{1-6}$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as $(C_{1-6}alkyl)_2amino$, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted. Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bond. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also includes carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with 1 or more halogen. Haloalkyl groups include perhaloalkyl groups, wherein all hydrogens of an alkyl group have been replaced with halogens (e.g., —$CF_3$, $CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term $C_3$-$C_6$ cyclic alkoxy refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as an unsaturated, aromatic monocyclic ring of 6 carbon members or to an unsaturated, aromatic polycyclic ring of from 10 to 14 carbon members. Aryl rings can be, for example, phenyl or naphthyl ring each optionally substituted with one or more moieties capable of replacing one or more hydrogen atoms. Non-limiting examples of aryl groups include: phenyl, naphthylen-1-yl, naphthylen-2-yl, 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups of the present invention are optionally substituted. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more ring having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-Dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be substituted. Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxyquinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R_2$ and $R_3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposed of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

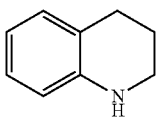

is, for the purposes of the present invention, considered a heterocyclic unit. 6,7-Dihydro-5H-cyclopentapyrimidine having the formula:

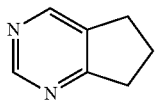

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

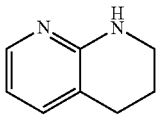

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted $C_1$ alkyl; trifluoromethyl is a substituted $C_1$ alkyl; 4-hydroxyphenyl is a substituted aromatic ring; (N,N-dimethyl-5-amino)octanyl is a substituted $C_8$ alkyl; 3-guanidinopropyl is a substituted $C_3$ alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine(I)), —CN, —NO$_2$, oxo (=O), —OR$^5$, —SR$^5$, —N(R$^5$)$_2$, —NR$^5$C(O)R$^5$, —SO$_2$R$^5$, —SO$_2$OR$^5$, —SO$_2$N(R$^5$)$_2$, —C(O)R$^5$, —C(O)OR$^5$, —C(O)N(R$^5$)$_2$, $C_{1-6}$ alkyl, $C_{1-6}$ haloalkyl, $C_{1-6}$ alkoxy, $C_{2-8}$ alkenyl, $C_{2-8}$ alkynyl, $C_{3-14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —NO$_2$, oxo, and R$^5$; wherein R$^5$, at each occurrence, independently is hydrogen, —OR$^6$, —SR$^6$, —C(O)R$^6$, —C(O)OR$^6$, —C(O)N(R$^6$)$_2$, —SO$_2$R$^6$, S(O)$_2$OR$^6$, —N(R$^6$)$_2$, —NR$^6$C(O)R$^6$, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^5$ units taken together with the atom(s) to which they are bound form an optionally substituted carbocycle or heterocycle wherein said carbocycle or heterocycle has 3 to 7 ring atoms; wherein R$^6$, at each occurrence, independently is hydrogen, $C_{1-6}$ alkyl, $C_{1-6}$ haloalkyl, $C_{2-8}$ alkenyl, $C_{2-8}$ alkynyl, cycloalkyl (e.g., $C_{3-6}$ cycloalkyl), aryl, heterocycle, or heteroaryl, or two R$^6$ units taken together with the atom(s) to which they are bound form an optionally substituted carbocycle or heterocycle wherein said carbocycle or heterocycle preferably has 3 to 7 ring atoms.

In some embodiments, the substituents are selected from
i) —OR$^7$; for example, —OH, —OCH$_3$, —OCH$_2$CH$_3$, —OCH$_2$CH$_2$CH$_3$;
ii) —C(O)R$^7$; for example, —COCH$_3$, —COCH$_2$CH$_3$, —COCH$_2$CH$_2$CH$_3$;
iii) —C(O)OR$^7$; for example, —CO$_2$CH$_3$, —CO$_2$CH$_2$CH$_3$, —CO$_2$CH$_2$CH$_2$CH$_3$;
iv) —C(O)N(R$^7$)$_2$; for example, —CONH$_2$, —CONHCH$_3$, —CON(CH$_3$)$_2$;
v) —N(R$^7$)$_2$; for example, —NH$_2$, —NHCH$_3$, —N(CH$_3$)$_2$, —NH(CH$_2$CH$_3$);
vi) halogen: —F, —Cl, —Br, and —I;
vii) —CH$_m$X$_n$; wherein X is halogen, m is from 0 to 2, m+n=3; for example, —CH$_2$F, —CHF$_2$, —CF$_3$, —CCl$_3$, or —CBr$_3$;
viii) —SO$_2$R$^7$; for example, —SO$_2$H; —SO$_2$CH$_3$; —SO$_2$C$_6$H$_5$;
ix) $C_1$-$C_6$ linear, branched, or cyclic alkyl;
x) Cyano
xi) Nitro;
xii) N(R$^7$)C(O)R$^7$;
xiii) Oxo (=O);
xiv) Heterocycle; and
xv) Heteroaryl.
wherein each R$^7$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two R$^7$ units can be taken together to form a ring comprising 3-7 ring atoms. In certain aspects, each R$^7$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the neuroprotective agent described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, $LiOH$, $NaOH$, $KOH$, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^7)_2$, each $R^7$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from which a patient is suspected to suffer.

As used herein, "therapeutically effective" and "effective dose" refer to a substance or an amount that elicits a desirable biological activity or effect.

As used herein, the term "neuroprotection" shall mean the protecting of neurons in the brain, central nervous system or peripheral nervous system from death and/or damage. Preferably, the neurons are protected from death or damage caused by oxidative stress or excess glutamate.

As used herein, the term "neuroprotective agent" shall mean a compound that provides neuroprotection.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The Neuroprotective Agents

The neuroprotective agents of the present invention are fluorinated sulfamides, and include all enantiomeric and diastereomeric forms and pharmaceutically accepted salts thereof having the formula:

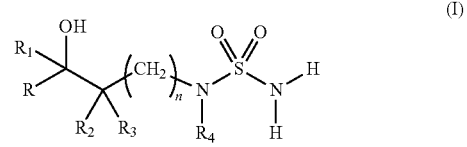

(I)

including hydrates, solvates, pharmaceutically acceptable salts, prodrugs and complexes thereof, wherein:

R is selected from the group consisting of optionally substituted aryl, optionally substituted benzoisoxazole, and optionally substituted benzothiophene where R may be substituted by 0-5 moieties;

n is 1 or 2;

$R^1$ is selected from the group consisting of hydrogen and optionally substituted $C_{1-6}$ alkyl;

$R^2$, $R^3$, and $R^4$ are each independently selected from the group consisting of hydrogen, halogen, and optionally substituted $C_{1-6}$ alkyl; and R¹ and R⁴ are taken together with atoms to which they are bound to form an optionally substituted ring having from 5 to 7 ring atoms.

In some embodiments R is phenyl optionally substituted with 1, 2 or 3 substituents independently selected from $C_{1-6}$ alkyl, halogen, $C_{1-6}$ alkoxy, OH, $NH_2$, $NH(C_{1-6}$ alkyl), $N(C_{1-6}$ alkyl)$_2$, $NO_2$, $C_{1-3}$ haloalkyl, $C_{1-3}$ haloalkoxy, SH, $SC_{1-6}$ alkyl, CN, and 3-10 membered cycloheteroalkyl containing 1 to 4 heteroatoms selected from N, O and S.

In some embodiments R is phenyl optionally substituted with 1, 2, 3, 4 or 5 substituents independently selected from fluorine, chlorine, trifluoromethyl, trifluoromethoxy, methyl and methoxy.

In some embodiments R is benzothiophene optionally substituted with 1, 2, 3, 4 or 5 substituents independently selected from $C_{1-6}$ alkyl, halogen, $C_{1-6}$ alkoxy, OH, $NH_2$, $NH(C_{1-6}$ alkyl), $N(C_{1-6}$ alkyl)$_2$, $NO_2$, $C_{1-3}$ haloalkyl, $C_{1-3}$ haloalkoxy, SH, $SC_{1-6}$ alkyl, CN, and 3-10 membered cycloheteroalkyl containing 1 to 4 heteroatoms selected from N, O and S.

In some embodiments R is benzothiophene optionally substituted with 1, 2, 3, 4 or substituents independently selected from fluorine, chlorine, trifluoromethyl, trifluoromethoxy, methyl and methoxy.

In some embodiments R is benzisoxazole optionally substituted with 1, 2, 3, or 4 substituents independently selected from $C_{1-6}$ alkyl, halogen, $C_{1-6}$ alkoxy, OH, $NH_2$, $NH(C_{1-6}$ alkyl), $N(C_{1-6}$ alkyl)$_2$, $NO_2$, $C_{1-3}$ haloalkyl, $C_{1-3}$ haloalkoxy, SH, $SC_{1-6}$ alkyl, CN, and 3-10 membered cycloheteroalkyl containing 1 to 4 heteroatoms selected from N, O and S.

In some embodiments R is benzisoxazole optionally substituted with 1, 2, 3, 4 or 5 substituents independently selected from fluorine, chlorine, trifluoromethyl, trifluoromethoxy, methyl and methoxy.

In some embodiments R is phenyl, 2-fluorophenyl, 3-fluorophenyl, 4-fluorophenyl, 2,4-difluorophenyl, 2,5-difluorophenyl, 2,6-difluorophenyl, 2-chlorophenyl, 2-bromophenyl, 2-trifluoromethylphenyl, 3-trifluoromethylphenyl, 2,6-dichlorophenyl, 2,4-dichlorophenyl, 2-methylphenyl, 2-ethylphenyl, 2-methoxyphenyl, 2-chloro-6-fluorophenyl, 2-chloro-4-fluorophenyl, 2-fluoro-6-methoxyphenyl, 4-fluoro-2-methoxyphenyl, or 2-chloro-6-methoxyphenyl.

In some embodiments R is benzothiophene.
In some embodiments R is benzisoxazole.
In some embodiments R¹ is H.
In some embodiments R¹ is optionally substituted $C_{1-6}$ alkyl.
In some embodiments R¹ is methyl.
In some embodiments R² is H.
In some embodiments R² is selected from $C_{1-6}$ alkyl.
In some embodiments R² is methyl.
In some embodiments R² is a halogen.
In some embodiments R³ is H.
In some embodiments R³ is selected from $C_{1-6}$ alkyl.
In some embodiments R³ is methyl.
In some embodiments R³ is a halogen.
In some embodiments n is 1.
In some embodiments n is 2.
In some embodiments R⁴ is H.
In some embodiments R⁴ is selected from $C_{1-6}$ alkyl.
In some embodiments R⁴ is a halogen.
In some embodiments, n is 1 and R¹ and R⁴ are taken together to form an optionally substituted ring containing from 5 to 7 ring atoms.
In some embodiments, n is 2 and R¹ and R⁴ are taken together to form an optionally substituted ring containing from 5 to 7 ring atoms.

Exemplary embodiments include compounds having the formula (I) or a pharmaceutically acceptable salt form thereof:

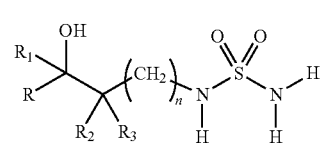

(I)

wherein non-limiting examples of R, R¹, R², R³ and "n" are defined herein below in Table 1.

TABLE 1

| Compound # | R | R¹ | R² | R³ | n |
|---|---|---|---|---|---|
| 1 | phenyl | H | H | H | 1 |
| 2 | 2-fluorophenyl | H | H | H | 1 |
| 3 | 2-fluorophenyl | methyl | H | H | 1 |
| 4 | 2-fluorophenyl | H | methyl | methyl | 1 |
| 5 | 2-fluorophenyl | H | H | H | 2 |
| 6 | 3-fluorophenyl | H | H | H | 1 |
| 7 | 4-fluorophenyl | H | H | H | 1 |
| 8 | 2,4-difluorophenyl | H | H | H | 1 |
| 9 | 2,5-difluorophenyl | H | H | H | 1 |
| 10 | 2,6-difluorophenyl | H | H | H | 1 |
| 11 | 2-chlorophenyl | H | H | H | 1 |
| 12 | 2-chlorophenyl | methyl | H | H | 1 |
| 13 | 2-chlorophenyl | H | H | H | 2 |
| 14 | 2-bromophenyl | H | H | H | 1 |
| 15 | 2-trifluoromethylphenyl | H | H | H | 1 |
| 16 | 3-trifluoromethylphenyl | H | H | H | 1 |
| 17 | 2,6-dichlorophenyl | H | H | H | 1 |
| 18 | 2,4-dichlorophenyl | H | H | H | 1 |
| 19 | 2-methylphenyl | H | H | H | 1 |
| 20 | 2-ethylphenyl | H | H | H | 1 |
| 21 | 2-methoxyphenyl | H | H | H | 1 |
| 22 | 2-chloro-4-fluorophenyl | H | H | H | 1 |
| 23 | 2-chloro-6-fluorophenyl | H | H | H | 1 |
| 24 | 2-fluoro-6-methoxyphenyl | H | H | H | 1 |
| 25 | 4-fluoro-2-methoxyphenyl | H | H | H | 1 |
| 26 | 2-chloro-6-methoxyphenyl | H | H | H | 1 |
| 27 | benzo[b]thiophen-3-yl | H | H | H | 1 |
| 28 | benzo[d]isoxazol-3-yl | H | H | H | 1 |

Exemplary embodiments include compounds having the formula (II) or a pharmaceutically acceptable salt form thereof:

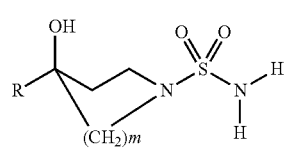

(II)

wherein R is preferably selected from the group consisting of optionally substituted aryl, optionally substituted benzoisoxazole, and optionally substituted benzothiophene where R may be substituted by 0-5 moieties, and "m" is preferably 1, 2 or 3. Non-limiting examples of R and "m" are defined herein below in Table 2.

TABLE 2

| Compound # | R | m |
|---|---|---|
| 29 | phenyl | 2 |
| 30 | 2-fluorophenyl | 1 |
| 31 | 2-fluorophenyl | 2 |
| 32 | 2-fluorophenyl | 3 |
| 33 | 4-fluorophenyl | 2 |
| 34 | 2,6-difluorophenyl | 2 |
| 35 | 2-chlorophenyl | 2 |
| 36 | 2-chlorophenyl | 3 |
| 37 | 2-trifluoromethylphenyl | 2 |
| 38 | 3-trifluoromethylphenyl | 2 |
| 39 | 2-methylphenyl | 2 |
| 40 | 2-methoxyphenyl | 2 |
| 41 | 2-fluoro-6-methoxyphenyl | 2 |
| 42 | benzo[b]thiophen-3-yl | 2 |
| 43 | benzo[d]isoxazol-3-yl | 2 |

For the purposes of demonstrating the manner in which the compounds of the present invention are named and referred to herein, the compound having the formula:

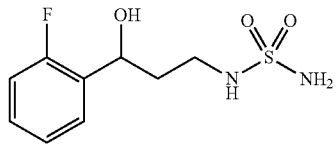 [SMILES: NS(=O)(=O)NCCC(O)c1ccccc1F]

has the chemical name 3-(2-fluoro-phenyl)-3-hydroxypropyl-1-sulfamide.

For the purposes of the present invention, a compound depicted by the racemic formula, for example:

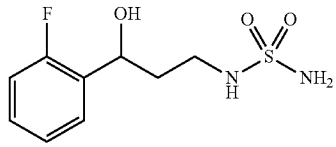 [SMILES: NS(=O)(=O)NCCC(O)c1ccccc1F]

will stand equally well for either of the two enantiomers having the formula:

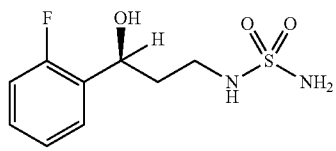 [SMILES: NS(=O)(=O)NCC[C@H](O)c1ccccc1F]

or the formula:

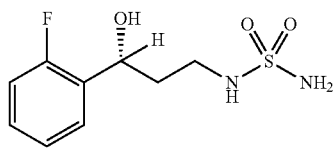

or mixtures thereof, or in the case where a second chiral center is present, all diastereomers.

For the purposes of demonstrating the manner in which the compounds of the present invention are named and referred to herein, the compound having the formula:

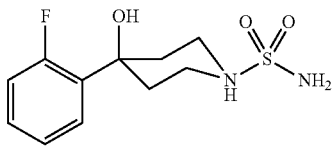 [SMILES: NS(=O)(=O)N1CCC(O)(c2ccccc2F)CC1]

has the chemical name 4-(2-Fluorophenyl)-4-hydroxypiperidine-1-sulfonamide.

In all of the embodiments provided herein, examples of suitable optional substituents are not intended to limit the scope of the claimed invention. The compounds of the invention may contain any of the substituents, or combinations of substituents, provided herein.

PROCESS

The present invention further relates to a process for preparing the neuroprotective agents of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis*, 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the General Synthetic Schemes:

GENERAL SYNTHETIC SCHEMES FOR PREPARATION OF COMPOUNDS

The reagents used in the preparation of the compounds of this invention can be either commercially obtained or can be prepared by standard procedures described in the literature. In accordance with this invention, compounds in the genus may be produced by one of the following reaction schemes.

Compounds of formula (I) may be prepared according to the process outlined in Scheme 1.

aluminum hydride and the like in an organic solvent such as tetrahydrofuran, dichloromethane and the like to yield the corresponding compound of formula (V).

A compound of formula (V) can then be converted into a hydroxyalkyl sulfamide compound of formula (I) via multiple pathways.

A compound of formula (V) can be treated with a suitable protected chlorosulfonylcarbamate (VI), formed in situ by the reaction of chlorosulfonylisocyanate and an alcohol such as tert-butyl alcohol, benzyl alcohol, ethanol and the like in an organic solvent like dichloromethane, chloroform and the like to yield the carbamate of a compound of formula (VII). The protecting group can be remove by treatment under suitable conditions such as 1) with acid, such as hydrogen chloride, trifluoroacetic acid, and the like in organic solvent such as 1,4-dioxane, dichloromethane, and the like, or 2) hydrogen in the presence of a catalyst such as palladium on activated carbon, platinum oxide and the like in an organic solvent such as ethyl acetate, methanol, ethanol or 3) base such as sodium hydroxide, potassium carbonate and the like in a solvent like water, methanol, tetrahydrofuran and the like to give a hydroxyalkyl sulfamide of formula (I).

Scheme 1

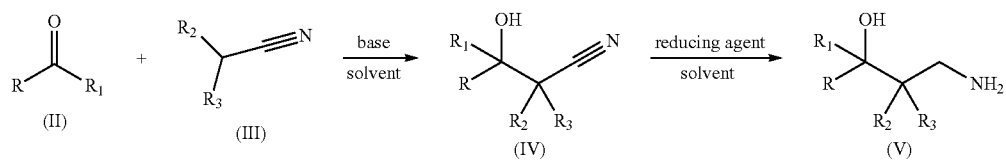

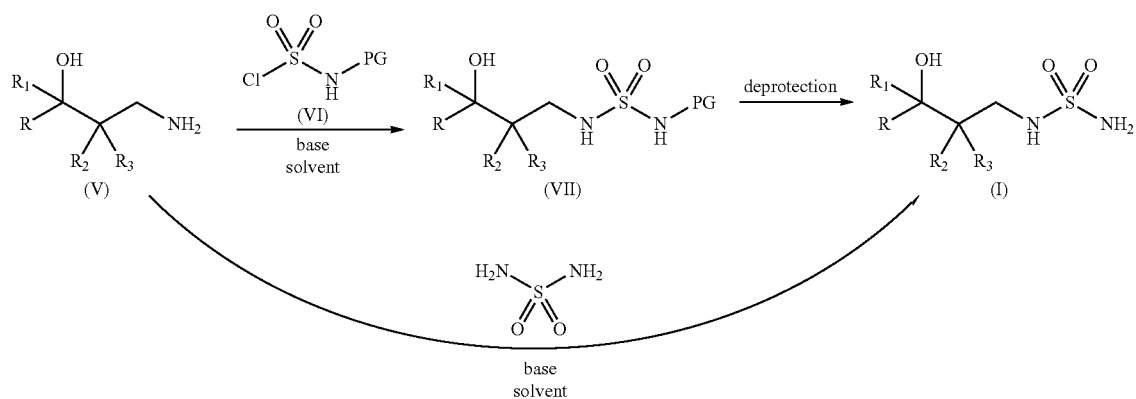

Accordingly, a suitably substituted compound of formula (II), a known compound or compound prepared by known methods, is reacted with the metalated species of a nitrile (III), prepared from the reaction of the nitrile (III) with a suitable base such as lithium diisopropylamide, sodium bis(trimethylsilyl)amide, and the like in an organic solvent such as tetrahydrofuran, ethyl ether and the like, to give the substituted hydroxypropionitrile (IV). This is then reduced in the presence of a reducing agent such as borane (as a complex with tetrahydrofuran, dimethylsulfide and the like), lithium Alternatively, treatment of a compound of formula (V) with sulfamide in the presence of a base, such as triethylamine, N-methylmorpholine, and the like, in an organic solvent such as ethanol, 1,4-dioxane and the like, at elevated temperatures such as between 40° C. and reflux, provides directly a hydroxyalkyl sulfamide of formula (I).

Compounds of formula (II) may be prepared according to the process outlined in Scheme 2.

Scheme 2

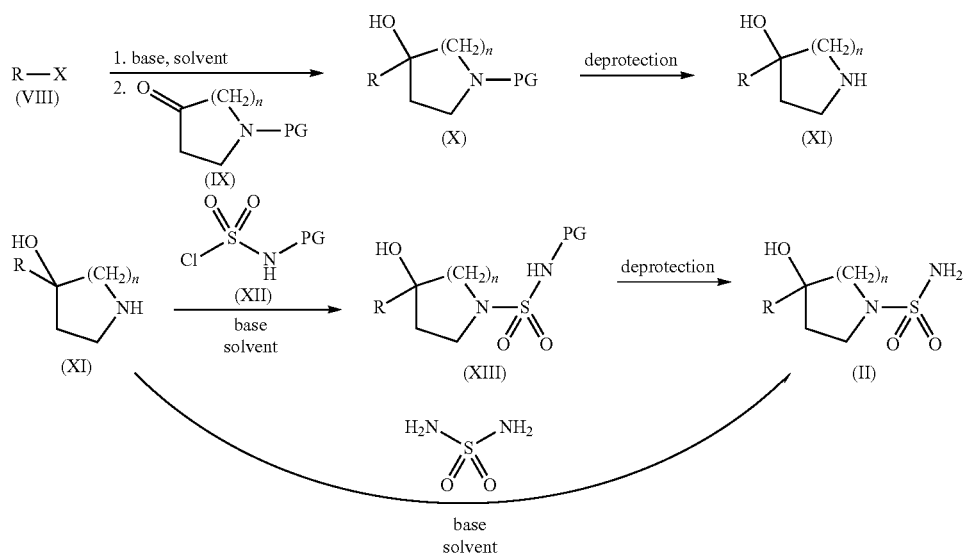

Accordingly, a suitably substituted compound, R—X (VIII), a known compound or compound prepared by known methods, is reacted with a strong base, such as butyllithium or isopropylmagnesium chloride and the like in an organic solvent like tetrahydrofuran, diethyl ether and the like, to give the metalated species. This is then reacted with a suitably substituted compound of formula (IX) to give the compound of formula (X). This can be deprotected by known methods to give compound of formula (XI).

A compound of formula (XI) can then be converted into a hydroxyalkyl sulfamide compound of formula (II) via multiple pathways.

A compound of formula (XI) can be treated with a suitable protected chlorosulfonylcarbamate (XII), formed in situ by the reaction of chlorosulfonylisocyanate and an alcohol such as tert-butyl alcohol, benzyl alcohol, ethanol and the like in an organic solvent like dichloromethane, chloroform and the like to yield the carbamate of a compound of formula (XIII). The protecting group can be remove by treatment under suitable conditions such as 1) with acid, such as hydrogen chloride, trifluoroacetic acid, and the like in organic solvent such as 1,4-dioxane, dichloromethane, and the like, or 2) hydrogen in the presence of a catalyst such as palladium on activated carbon, platinum oxide and the like in an organic solvent such as ethyl acetate, methanol, ethanol or 3) base such as sodium hydroxide, potassium carbonate and the like in a solvent like water, methanol, tetrahydrofuran and the like to give a hydroxyalkyl sulfamide of formula (II).

Alternatively, treatment of a compound of formula (XI) with sulfamide in the presence of a base, such as triethylamine, N-methylmorpholine, and the like, in an organic solvent such as ethanol, 1,4-dioxane and the like, at elevated temperatures such as between 40° C. and reflux, provides directly a hydroxyalkyl sulfamide of formula (II).

The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

$^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm.

EXAMPLES

Examples 1 through 19 provide methods for preparing representative compounds of formula (I). The skilled practitioner will know how to substitute the appropriate reagents, starting materials and purification methods known to those skilled in the art, in order to prepare additional compounds of the present invention.

Example 1

Synthesis of 3-(2-Chloro-phenyl)-3-hydroxypropyl-1-sulfamide

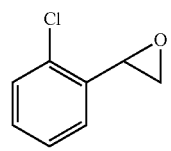

2-(2-Chloro-phenyl)-oxirane.

2-Chloro-benzaldehyde (5 mL, 44 mmol) was dissolved in dichloromethane (45 mL) and treated with trimethylsulfonium iodide (10.25 g, 49.28 mmol) and aqueous sodium hydroxide solution (50%, 44 g) subsequently. The mixture was stirred vigorously at room temperature for overnight. The organic phase was separated and concentrated to give clear oil, which was stored in the refrigerator and used directly without further purification.

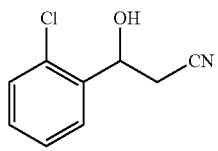 [SMILES: N#CCC(O)c1ccccc1Cl]

3-(2-Chloro-phenyl)-3-hydroxypropionitrile.

2-(2-chloro-phenyl)-oxirane (440 mg, 2.85 mmol) was dissolved in ethanol (3 mL) and treated with potassium cyanide in water (3 mL) and hydrogen chloride (4 M in 1,4-dioxane, 0.71 mL) subsequently. The mixture was stirred at 50° C. for 8 hr and room temperature for overnight. Saturated sodium hydrogen carbonate was added and the mixture was concentrated. The residue was extracted with ethyl acetate. The organic layer was concentrated and purified by column chromatography (40 g silica gel cartridge) eluting with ethyl acetate/hexane (0%-30%) to give the product as a colorless oil (330 mg, 64%). $^1$H NMR (CDCl$_3$) δ 7.70-7.60 (m, 1H), 7.40-7.20 (m, 2H), 5.50-5.40 (m, 1H), 2.98-2.85 (m, 1H), 2.85-2.80 (m, 1H), 2.78-2.65 (m, 1H).

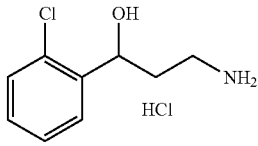 [SMILES: NCCC(O)c1ccccc1Cl ; Cl]

3-Amino-1-(2-chloro-phenyl)-propan-1-ol hydrochloride salt.

3-(2-Chloro-phenyl)-3-hydroxy-propionitrile (740 mg, 4.07 mmol) was slowly treated with a solution of borane-tetrahydrofuran complex (9 mL, 8.96 mmol, 1M in tetrahydrofuran) at 0° C. After bubbling ceased, the reaction mixture was heated to 75° C. for 2 hours and 1.1 eq of additional borane was added to drive the reaction to completion. The reaction mixture was concentrated. The white solid obtained was treated with methanol (14 mL), followed by hydrogen chloride (2M in diethyl ether, 14 mL). The resulting mixture was heated to reflux for 2 hours, allowed to cool to ambient temperature and then concentrated at reduced pressure. To the residue was added aqueous hydrochloric acid (10 mL, 1 N) followed by diethyl ether (20 mL). The aqueous layers were separated and concentrated at reduced pressure and dried to give the product as a white solid (796 mg, 88%).

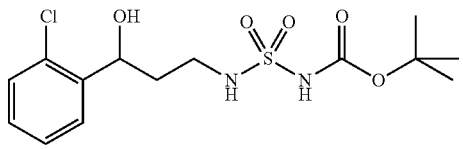 [SMILES: CC(C)(C)OC(=O)NS(=O)(=O)NCCC(O)c1ccccc1Cl]

3-(2-Chloro-phenyl)-3-hydroxypropyl-1-sulfamide carbamic acid tert-butyl ester.

To a solution of chlorosulfonyl isocyanate (0.31 mL, 3.58 mmol) in dichloromethane (6 mL) at 3° C. was added tert-butanol (0.34 mL, 3.58 mmol). After 25 minutes, pyridine (0.64 mL, 7.88 mmol) was added and the resulting mixture was stirred for 40 minutes during which time a precipitate formed. This slurry was added via pipette to a mixture of 3-amino-1-(2-chloro-phenyl)-propan-1-ol hydrochloride salt (796 mg, 3.58 mmol) and triethyl amine (1.25 mL, 8.95 mmol) in dichloromethane (6 mL) at 3° C. The resulting mixture was allowed to warm to ambient temperature over 4 hours. The reaction mixture was diluted with dichloromethane (30 mL) and washed with dilute hydrochloric acid (30 mL, 0.1 N) followed by saturated aqueous sodium chloride (50 mL). The organic layer was concentrated at reduce pressure. The residue was purified by column chromatography (80 g silica gel cartridge) eluting with ethyl acetate/hexane (20%-60%) to give the product as a white solid (886 mg, 68%). $^1$H NMR (DMSO-d6) δ 10.79 (s, 1H), 7.60-7.20-(m, 4H), 5.50 (d, J=4.5 Hz, 1H), 5.00-4.80 (m, 1H), 3.20-2.90 (m, 2H), 1.98-1.78 (m, 1H), 1.78-1.55 (m, 1H), 1.20 (s, 9H).

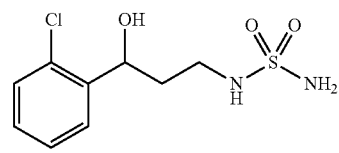

3-(2-Chloro-phenyl)-3-hydroxypropyl-1-sulfamide.

To N-[3-(2-Chloro-phenyl)-3-hydroxy-1-carbamic tert-butyl ester-propyl]-sulfamide (886 mg, 2.43 mmol) in methanol (10 mL) was added hydrogen chloride (4M, 10 mL), and the resulting solution was stirred for 16 hours. The reaction mixture was concentrated at reduced pressure and the resulting solid was purified by crystallized from hot dichloromethane to give the product as a white solid (580 mg, 90%). $^1$H NMR (DMSO-d6) δ 7.62-7.55 (m, 1H), 7.40-7.32 (m, 2H,), 7.32-7.20 (m, 1H), 6.48 (s, 2H), 6.44 (t, J=7.1 Hz, 1H), 5.43 (d, J=4.7 Hz, 1H), 5.00-4.88 (m, 1H), 3.10-2.90 (m, 2H), 1.96-1.82 (m, 1H), 1.8-1.62 (m, 1H); LC-MS for C9H13ClN2O3S: t=3.14 min. (M—H$_2$O$^+$H)$^+$ at 247.01.

Example 2

Synthesis of 3-Benzo[b]thiophen-3-yl-3-hydroxypropyl-1-sulfamide

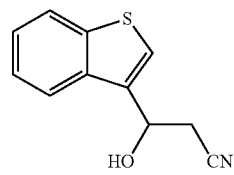 [SMILES: N#CCC(O)c1csc2ccccc12]

3-Benzo[b]thiophen-3-yl-3-hydroxy-propionitrile.

To a stirring solution of diisopropylamine (0.93 mL, 6.58 mmol) in tetrahydrofuran (8 mL) at −78° C. under nitrogen was added a solution of n-butyllithium (2.75 mL, 6.88 mmol, 2.5 M in hexane). After the addition was complete, the mixture was stirred at −78° C. for 10 minutes and removed cooling bath for 5 minutes. The mixture was cooled back to −78° C., acetonitrile (0.31 mL, 5.98 mmol) was added and the reaction mixture was then stirred at −78° C. for 30 minutes. Benzo[b]thiophene-3-carbaldehyde (1 g, 5.98 mmol) in tetrahydrofuran (4 mL) was added and the resulting solution was allowed to warm to ambient temperature. After 18 hours at ambient temperature, saturated aqueous ammonium chloride (5 mL) was added to the reaction mixture and it was concentrated at reduced pressure. The resulting crude product was diluted with ethyl acetate (20 mL), washed with water (10 mL) followed by saturated aqueous sodium chloride (10 mL).

The organic layer was concentrated and purified by column chromatography (80 g silica gel cartridge) eluting with ethyl acetate/hexane (30%-50%) to give the product as a light yellow oil (1.2 g, 99%).

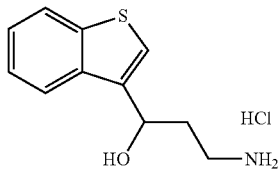 [SMILES: NCCC(O)c1csc2ccccc12 ; Cl]

3-Amino-1-benzo[b]thiophen-3-yl-propan-1-ol hydrochloride salt.

3-Benzo[b]thiophen-3-yl-3-hydroxy-propionitrile (1.2 g, 5.90 mmol) was slowly treated with a solution of borane-tetrahydrofuran complex (13 mL, 12.98 mmol, 1M in tetrahydrofuran) at 0° C. After bubbling ceased, the reaction mixture was heated to 75° C. for 2 hours and 6.0 eq of additional borane was added to drive the reaction to completion. The reaction mixture was concentrated. The white solid obtained was treated with methanol (14 mL), followed by hydrogen chloride (2M in diethyl ether, 43 mL). The resulting mixture was heated to reflux for 2 hours, allowed to cool to ambient temperature and then concentrated at reduced pressure. To the residue was added aqueous hydrochloric acid (10 mL, 1 N) followed by diethyl ether (20 mL). The aqueous layers were separated and concentrated at reduced pressure to give the product as a yellow solid (840 mg, 58%).

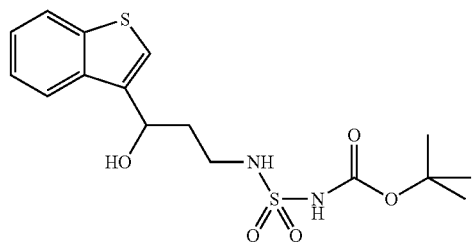 [SMILES: CC(C)(C)OC(=O)NS(=O)(=O)NCCC(O)c1csc2ccccc12]

3-Benzo[b]thiophen-3-yl-3-hydroxypropyl-1-sulfamide carbamic acid tert-butyl ester.

To a solution of chlorosulfonyl isocyanate (0.17 mL, 1.97 mmol) in dichloromethane (4 mL) at 3° C. was added tert-butanol (0.19 mL, 1.97 mmol). After 25 minutes, pyridine (0.35 mL, 4.33 mmol) was added and the resulting mixture was stirred for 40 minutes during which time a precipitate formed. This slurry was added via pipette to a mixture of 3-Amino-1-benzo[b]thiophen-3-yl-propan-1-ol hydrochloride salt (480 mg, 1.97 mmol) and triethyl amine (0.67 mL, 4.92 mmol) in dichloromethane (4 mL) at 3° C. The resulting mixture was allowed to warm to ambient temperature over 4 hours. The reaction mixture was diluted with dichloromethane (30 mL) and washed with dilute hydrochloric acid (30 mL, 0.1 N) followed by saturated aqueous sodium chloride (50 mL). The organic layer was concentrated at reduce pressure. The residue was purified by column chromatography (40 g silica gel cartridge) eluting with ethyl acetate/hexane (10%-40%) to give the product as a white solid (440 mg, 59%). LC-MS for $C_{16}H_{22}N_2O_5S_2$: t=5.78 min. (M-Boc-$H_2O^+H)^+$ at 269.0.

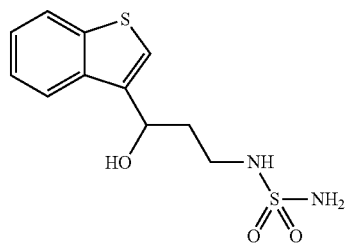 [SMILES: NS(=O)(=O)NCCC(O)c1csc2ccccc12]

3-Benzo[b]thiophen-3-yl-3-hydroxypropyl-1-sulfamide.

To 3-Benzo[b]thiophen-3-yl-3-hydroxy-1-Carbamic acid tert-butyl ester sulfamide (440 mg, 1.14 mmol) in ethyl acetate (5.7 mL) was added hydrogen chloride (4M, 5.7 mL), and the resulting solution was stirred for 16 hours. The reaction mixture was concentrated at reduced pressure and the residue was purified by preparative TLC with a mixture of ethyl acetate and hexanes (1:1) to give the product as a clear oil (104.2 mg, 32%). $^1$H NMR (DMSO-$d_6$) δ 8.00-7.90 (m, 2H), 7.53 (s, 1H), 7.42-7.35 (m, 2H), 6.60-6.40 (m, 3H), 5.41 (d, J=4.7 Hz, 1H), 5.10-4.90 (m, 1H), 3.10-2.90 (m, 2H), 2.10-1.90 (m, 2H); LC-MS for C11H14N2O3S2: t=3.53 min. (M-$H_2O+H)^+$ at 268.94.

Example 3

Synthesis of 3-(2-Chloro-phenyl)-3-hydroxybutanyl-1-sulfamide

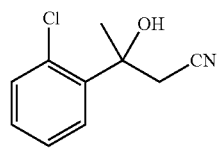

3-(2-Chloro-phenyl)-3-hydroxy-butyronitrile.

To a stirring solution of diisopropylamine (0.97 mL, 6.83 mmol) in tetrahydrofuran (15 mL) at −78° C. under nitrogen was added a solution of n-butyllithium (2.86 mL, 7.14 mmol, 2.5 M in hexane). After the addition was complete, the mixture was stirred at −78° C. for 10 minutes and removed cooling bath for 5 minutes. The mixture was cooled back to −78° C., acetonitrile (0.33 mL, 6.21 mmol) was added and the reaction mixture was then stirred at −78° C. for 30 minutes. 1-(2-Chloro-phenyl)-ethanone (1 mL, 7.45 mmol) was added and the resulting solution was allowed to warm to ambient temperature. After 18 hours at ambient temperature, saturated aqueous ammonium chloride (5 mL) was added to the reaction mixture and it was concentrated at reduced pressure. The resulting crude product was diluted with ethyl acetate (30 mL), washed with water (15 mL) followed by saturated aqueous sodium chloride (10 mL). The organic layer was concentrated and purified by column chromatography (40 g silica gel cartridge) eluting with ethyl acetate/hexane (0%-15%) to give the product as a colorless oil (1.1 g, 90%).

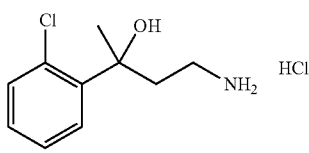

4-Amino-2-(2-chloro-phenyl)-butan-2-ol hydrochloride salt.

3-(2-Chloro-phenyl)-3-hydroxy-butyronitrile (1.1 g, 5.62 mmol) was slowly treated with a solution of borane-tetrahydrofuran complex (12.4 mL, 12.4 mmol, 1M in tetrahydrofuran) at 0° C. After bubbling ceased, the reaction mixture was heated to 70° C. for 3 hours. The reaction mixture was then concentrated. The white solid obtained was treated with methanol (12.4 mL), followed by hydrogen chloride (2M in diethyl ether, 12.4 mL). The resulting mixture was heated to reflux for 2 hours, allowed to cool to ambient temperature and then concentrated at reduced pressure. The solid obtained was triturated with diethyl ether and dried in vacuum oven to provide a light yellow solid (1.13 g, 85%).

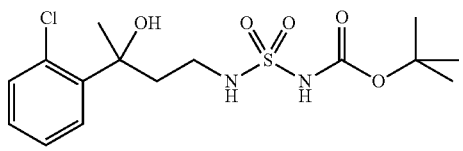 [SMILES: CC(C)(C)OC(=O)NS(=O)(=O)NCCC(C)(O)c1ccccc1Cl]

N-[3-(2-Chloro-phenyl)-3-hydroxybutanyl-1-sulfamide carbamic acid tert-butyl ester.

To a solution of chlorosulfonyl isocyanate (0.42 mL, 4.78 mmol) in dichloromethane (10 mL) at 3° C. was added tert-butanol (0.46 mL, 4.78 mmol). After 25 minutes, pyridine (0.85 mL, 10.52 mmol) was added and the resulting mixture was stirred for 40 minutes during which time a precipitate formed. This slurry was added via pipette to a mixture of 4-Amino-2-(2-chloro-phenyl)-butan-2-ol hydrochloride salt (1.13 g, 4.78 mmol) and triethyl amine (1.66 mL, 11.95 mmol) in dichloromethane (10 mL) at 3° C. The resulting mixture was allowed to warm to ambient temperature over 4 hours. The reaction mixture was diluted with dichloromethane (30 mL) and washed with aqueous potassium hydrogen sulfate (20 mL, 10%) followed by saturated aqueous sodium chloride (50 mL). The organic layer was concentrated at reduce pressure. The residue was purified by column chromatography (80 g silica gel cartridge) eluting with ethyl acetate/hexane (20%-50%) to give the product as an oil (1.0 g, 55%). LC-MS for $C_{15}H_{23}ClN_2O_5S$: t=5.11 min. (M+Na)$^+$ at 400.96.

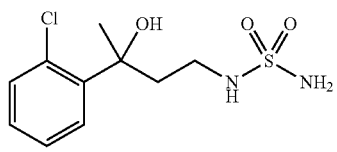 [SMILES: CC(O)(CCNS(N)(=O)=O)c1ccccc1Cl]

3-(2-Chloro-phenyl)-3-hydroxybutanyl-1-sulfamide.

To N-[3-(2-Chloro-phenyl)-3-hydroxy-1-carbamic acid tert-butyl ester butanyl]-sulfamide (1.0 g, 2.64 mmol) in methanol (10 mL) was added hydrogen chloride (4M, 10 mL), and the resulting solution was stirred for 16 hours. The reaction mixture was concentrated at reduced pressure and the resulting solid was purified by column chromatography (12 g silica gel cartridge) eluting with ethyl acetate/hexane (30%-60%) to give the product as white solid (494 mg, 67%). 1H NMR (DMSO-d6) δ 7.82-7.72 (m, 1H), 7.40-7.20 (m, 3H), 6.38 (s, 2H), 6.25 (t, J=7.1 Hz, 1H), 5.36 (s, 1H), 2.98-2.80 (m, 1H), 2.60-2.30 (m, 2H), 2.08-1.90 (m, 1H), 1.59 (s, 3H); LC-MS for C10H15ClN2O3S: t=3.58 min. (M–H$_2$O+H)$^+$ at 261.02.

Example 4

Synthesis of 3-(2,4-Difluoro-phenyl)-3-hydroxypropyl-1-sulfamide

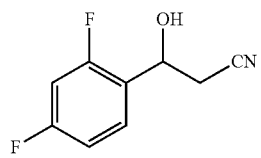 [SMILES: N#CCC(O)c1ccc(F)cc1F]

3-(2,4-Difluoro-phenyl)-3-hydroxy-propionitrile.

To a stirring solution of diisopropylamine (0.97 mL, 6.89 mmol) in tetrahydrofuran (15 mL) at –70° C. under nitrogen was added a solution of n-butyllithium (2.88 mL, 7.20 mmol, 2.5 M in hexane). After the addition was complete, the mixture was stirred at –70° C. for 10 minutes and removed cooling bath for 5 minutes. The mixture was cooled back to –70° C., acetonitrile (0.33 mL, 6.26 mmol) was added and the reaction mixture was then stirred at –70° C. for 30 minutes. 2,4-difluoro-benzaldehyde (1.09 g, 7.52 mmol) was added and the resulting solution was allowed to warm to ambient temperature. After 4 hours at ambient temperature, saturated aqueous ammonium chloride (5 mL) was added to the reaction mixture and it was concentrated at reduced pressure. The resulting crude product was diluted with ethyl acetate (25 mL), washed with water (10 mL) followed by saturated aqueous sodium chloride (10 mL). The organic layer was concentrated and purified by column chromatography (40 g silica gel cartridge) eluting with ethyl acetate/hexane (0%-10%) to give the product as light yellow oil (960 mg, 70%).

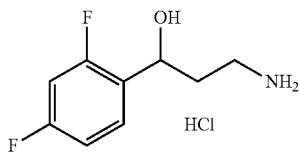 [SMILES: NCCC(O)c1ccc(F)cc1F ; Cl]

3-Amino-1-(2,4-difluoro-phenyl)-propan-1-ol hydrochloride salt.

3-(2,4-Difluoro-phenyl)-3-hydroxy-propionitrile (960 mg, 5.24 mmol) was slowly treated with a solution of borane-tetrahydrofuran complex (11.53 mL, 11.53 mmol, 1M in tetrahydrofuran) at 0° C. After bubbling ceased, the reaction mixture was heated to 70° C. for 3 hours. The reaction mixture was then concentrated. The white solid obtained was treated with methanol (11.5 mL), followed by HCl (2M in ether, 11.5 mL). The resulting mixture was heated to reflux for 2 hours, allowed to cool to ambient temperature and then concentrated at reduced pressure. The white solid obtained was triturated with diethyl ether and dried in vacuum oven to provide a white solid (1.10 g, 94%). LC-MS: t=2.20 min, (M+H)$^+$ at 188.08.

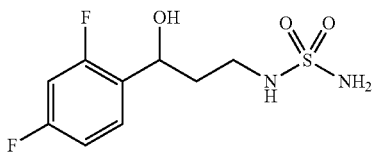 [SMILES: NS(=O)(=O)NCCC(O)c1ccc(F)cc1F]

3-(2,4-Difluoro-phenyl)-3-hydroxypropyl-1-sulfamide.

A mixture of 3-Amino-1-(2,4-difluoro-phenyl)-propan-1-ol hydrochloride salt (1.1 g, 4.92 mmol), sulfamide (945.46 mg, 9.84 mmol), and triethyl amine (2.06 mL, 14.76 mmol) in 1,4-dioxane (20 mL) was heated at 105° C. for 18 hours. After cooling to room temperature, the reaction mixture was concentrated and then partitioned between ethyl acetate (30 mL) and water (30 mL). The organic layer was dried (anhydrous magnesium sulfate), concentrated and purified by column chromatography (80 g silica gel cartridge) eluting with ethyl acetate/hexane (10%-50%) to give the product as an oil, which solidified when treated with chloroform. A white solid (300 mg, 23%) was obtained. $^1$H NMR (DMSO-d$_6$) δ 7.60-7.48 (m, 1H), 7.25-7.00 (m, 2H), 6.49 (s, 2H), 6.42 (t, J=7.1 Hz, 1H), 5.42 (d, J=4.7 Hz, 1H), 4.93-4.80 (m, 1H), 3.10-2.90 (m, 2H), 1.89-1.70 (m, 2H).

Example 5

Synthesis of 3-(2-Fluoro-phenyl)-3-hydroxy-2,2-dimethylpropyl-1-sulfamide

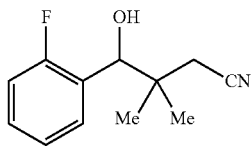 [SMILES: CC(C)(CC#N)C(O)c1ccccc1F]

3-(2-Fluoro-phenyl)-3-hydroxy-2,2-dimethyl-propionitrile.

To a stirring solution of diisopropylamine (2.27 mL, 16.1 mmol) in tetrahydrofuran (60 mL) at –20° C. under nitrogen was added a solution of n-butyllithium (7.1 mL, 17.7 mmol, 2.5 M in hexane). After the addition was complete, the mixture was cooled to –70° C., isobutyryl nitrile (1.46 mL, 16.1 mmol) was added and the reaction mixture was then warmed to –10° C. After 10 minutes, 2-fluoro-benzaldehyde (1.70 mL, 16.1 mmol) was added and the resulting solution was allowed to warm to ambient temperature. After one hour at ambient temperature, water (5 mL) was added to the reaction mixture and it was concentrated at reduced pressure. The resulting crude product was diluted with ethyl acetate (125 mL), washed with water (75 mL) followed by saturated aqueous sodium chloride (50 mL) and the organic layer was concentrated at reduced pressure to give the product as a colorless oil (3.1 g, ~100%). $^1$H NMR (CDCl$_3$) δ 7.70 (m, 1H), 7.35 (m, 1H), 7.22 (m, 1H), 7.04 (m, 1H), 4.99 (br s, 1H), 2.42 (br s, 1H), 1.24 (s, 6H).

3-Amino-1-(2-fluoro-phenyl)-2,2-dimethyl-propan-1-ol.
To a stirring solution of 3-(2-fluoro-phenyl)-3-hydroxy-2,2-dimethyl-propionitrile (1.5 g, 7.76 mmol) in tetrahydrofuran was added a solution of borane-tetrahydrofuran complex (17 mL, 17.0 mmol, 1M in tetrahydrofuran). After bubbling ceased, the reaction mixture was heated to 75° C. for 4 hours and then allowed to cool to ambient temperature. Methanol (9 mL) was added dropwise followed by hydrogen chloride (9 mL, 4N in 1,4-dioxane). The resulting mixture was heated to reflux for 2 hours, allowed to cool to ambient temperature and then concentrated at reduced pressure. To the residue was added aqueous hydrochloric acid (5 mL, 1 N) followed by ethyl acetate (20 mL). The layers were separated and the aqueous layer was basified with aqueous lithium hydroxide (6 mL, 1 N) and this aqueous phase was extracted with dichloromethane (3×75 mL). The organic extracts were combined, washed with saturated aqueous sodium chloride (20 mL) and concentrated at reduced pressure to give the product as a colorless oil (1.3 g, 85%). $^1$H NMR (CDCl$_3$) δ 7.53 (m, 1H), 7.25-7.05 (m, 2H), 6.94 (m, 1H), 5.06 (br s, 1H), 2.83 (q, J=12.5 Hz, 2H), 0.86 (d, J=8.5 Hz, 6H).

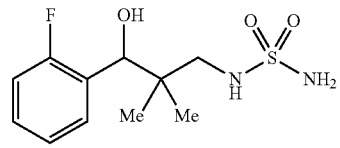 [SMILES: CC(C)(CNS(N)(=O)=O)C(O)c1ccccc1F]

3-(2-Fluoro-phenyl)-3-hydroxy-2,2-dimethylpropyl-1-sulfamide.

To a solution of chlorosulfonyl isocyanate (0.44 mL, 5.07 mmol) in dichloromethane (12 mL) at 3° C. was added tert-butanol (0.48 mL, 5.07 mmol). After 25 minutes, pyridine (0.90 mL, 11.2 mmol) was added and the resulting mixture was stirred for 40 minutes during which time a precipitate formed. This slurry was added via pipette to a solution of 3-amino-1-(2-fluoro-phenyl)-2,2-dimethyl-propan-1-ol (1.0 g, 5.07 mmol) in dichloromethane (12 mL) at 3° C. The resulting mixture was allowed to warm to ambient temperature over 4 hours. The reaction mixture was diluted with dichloromethane (100 mL) and washed with dilute hydrochloric acid (50 mL, 0.1 N) followed by saturated aqueous sodium chloride (50 mL). The organic layer was concentrated at reduce pressure. The resulting oil was dissolved in ethyl acetate (8 mL) and to this solution was added hydrogen chloride (20 mL, 4N in 1,4-dioxane) and the resulting solution was stirred for 16 hours. The reaction mixture was concentrated at reduced pressure and the resulting solid was purified by column chromatography through a silica gel cartridge (24 g) eluting with ethyl acetate/hexane (1:9 to 1:1) to give the product as a white solid (648 mg, 46% over 2 steps). $^1$H NMR (DMSO-d$_6$) δ 7.48 (m, 1H), 7.28 (m, 1H,), 7.22-7.05 (m, 2H), 6.44 (s, 2H), 6.24 (t, J=7.1 Hz, 1H), 5.35 (d, J=4.7 Hz, 1H), 4.75 (d, J=4.7 Hz, 1H), 2.86 (ddd, J=18.0, 7.0, 5.6 Hz, 2H), 0.79 (br s, 6H).

Example 6

Synthesis of 3-(2-Fluoro-phenyl)-3-hydroxypropyl-1-sulfamide

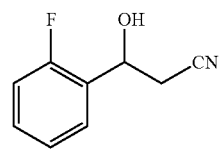

(2-Fluoro-phenyl)-hydroxypropionitrile.
To a stirring solution of diisopropylamine (5.95 mL, 42.7 mmol) in tetrahydrofuran (100 mL) at –70° C. under nitrogen was added a solution of n-butyllithium (17.6 mL, 44 mmol, 2.5 M in hexane). After the addition was complete, the mixture was stirred at −70° C. for 10 minutes and removed cooling bath for 5 minutes. The mixture was cooled back to −70° C., acetonitrile (2 mL, 38.1 mmol) was added and the reaction mixture was then stirred at −70° C. for 30 minutes. 2-fluorobenzaldehyde (5 mL, 47.4 mmol) was added and the resulting solution was allowed to warm to ambient temperature. After 18 hours at ambient temperature, saturated aqueous ammonium chloride (5 mL) was added to the reaction mixture and it was concentrated at reduced pressure. The resulting crude product was diluted with ethyl acetate (125 mL), washed with water (75 mL) followed by saturated aqueous sodium chloride (50 mL). The organic layer was concentrated and purified by column chromatography (80 g silica gel cartridge) eluting with ethyl acetate/hexane (10%-30%) to give the product as a colorless oil (6.5 g, 83%).

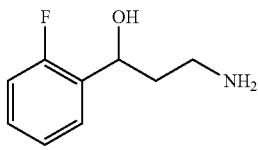 [SMILES: NCCC(O)c1ccccc1F]

3-Amino-1-(2-fluoro-phenyl)-propan-1-ol.

To a stirring solution of (2-fluoro-phenyl)-hydroxy-acetonitrile (5 g, 30.2 mmol) in tetrahydrofuran (20 mL) was slowly added a solution of borane-tetrahydrofuran complex (67 mL, 67.0 mmol, 1M in tetrahydrofuran). After bubbling ceased, the reaction mixture was heated to 75° C. for 2 hours and then allowed to cool to ambient temperature and concentrated. Methanol (30 mL) was added dropwise followed by hydrogen chloride (33 mL, 133 mmol, 4N in 1,4-dioxane). The resulting mixture was heated to reflux for 2 hours, allowed to cool to ambient temperature and then concentrated at reduced pressure. To the residue was added aqueous hydrochloric acid (10 mL, 1 N) followed by ethyl acetate (30 mL). The layers were separated and the aqueous layer was basified with sodium carbonate until pH>10 and this aqueous phase was mixed with brine (40 mL) and extracted dichloromethane (3×75 mL). The organic extracts were combined, dried (anhydrous magnesium sulfate) and concentrated at reduced pressure to give the product as a colorless oil (4.2 g, 82%).

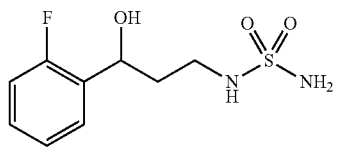 [SMILES: NS(=O)(=O)NCCC(O)c1ccccc1F]

3-(2-Fluoro-phenyl)-3-hydroxypropyl-1-sulfamide.

A mixture of 3-amino-1-(2-fluoro-phenyl)-propan-1-ol (1.8 g, 11.1 mmol) and sulfamide (2.05 g, 21.1 mmol) in 1,4-dioxane (20 mL) was heated at 110° C. for 24 hours. After cooling to room temperature, the reaction mixture was partitioned between ethyl acetate (30 mL) and water (30 mL). The organic layer was dried (anhydrous magnesium sulfate), concentrated and purified by column chromatography (80 g silica gel cartridge) eluting with ethyl acetate/hexane (30%-80%) to give the product as a white solid (685 mg, 26%). $^1$H NMR (DMSO-$d_6$) δ 7.53-7.48 (m, 1H), 7.32-7.08 (m, 3H), 6.49 (s, 2H), 6.40 (t, J=7.1 Hz, 1H), 5.38 (d, J=4.7 Hz, 1H), 4.93-4.86 (m, 1H), 3.05-2.90 (m, 2H), 1.89-1.79 (m, 2H).

Example 7

Synthesis of 3-(2,5-Difluoro-phenyl)-3-hydroxypropyl-1-sulfamide

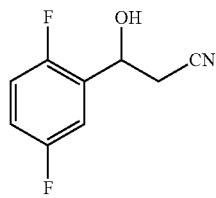 [SMILES: N#CCC(O)c1cc(F)ccc1F]

3-(2,5-Difluoro-phenyl)-3-hydroxypropionitrile was prepared by the same procedure of 3-(2-fluoro-phenyl)-3-hydroxy-propionitrile in example 6.

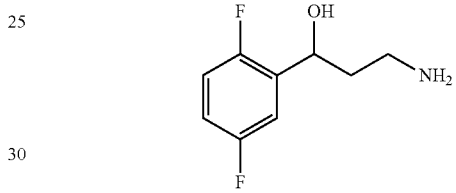

3-Amino-1-(2,5-difluoro-phenyl)-propan-1-ol was prepared by the same procedure of 3-amino-1-(2-fluoro-phenyl)-propan-1-ol in example 6.

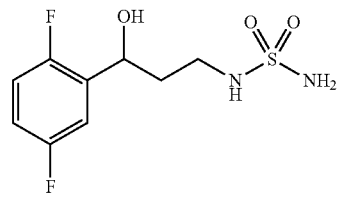 [SMILES: NS(=O)(=O)NCCC(O)c1cc(F)ccc1F]

3-(2,5-Difluoro-phenyl)-3-hydroxypropyl-1-sulfamide.

To a solution of chlorosulfonyl isocyanate (0.12 mL, 1.34 mmol) in dichloromethane (6 mL) at 3° C. was added tert-butanol (0.13 mL, 1.34 mmol). After 25 minutes, pyridine (0.24 mL, 2.95 mmol) was added and the resulting mixture was stirred for 40 minutes during which time a precipitate formed. This slurry was added via pipette to a solution of 3-amino-1-(2,5-difluoro-phenyl)-propan-1-ol (250 mg, 1.34 mmol) in dichloromethane (2 mL) at 3° C. The resulting mixture was allowed to warm to ambient temperature over 4 hours. The reaction mixture was diluted with ethyl acetate (30 mL) and washed with 10% potassium hydrogen sulfate in water (10 mL), water (10 mL, 0.1N) followed by saturated aqueous sodium chloride (20 mL). The organic layer was concentrated at reduce pressure. The resulting oil was dissolved in methanol (2 mL) and to this solution was added hydrogen chloride (3 mL, 4N in 1,4-dioxane) and the resulting solution was stirred for 2 hours. The reaction mixture was concentrated at reduced pressure and the resulting solid was purified by column chromatography through a silica gel cartridge (12 g) eluting with ethyl acetate/hexane (20% to 70%)

to give the product as a colorless oil that crystallized on standing (68.5 mg, 19% over 2 steps). ¹H NMR (DMSO-d₆) δ 7.29-7.08 (m, 3H), 6.48 (s, 2H), 6.12 (t, J=7.1 Hz, 1H), 5.50 (d, J=4.7 Hz, 1H), 4.91-4.83 (m, 1H), 3.01-2.92 (m, 2H), 1.86-1.76 (m, 2H).

Example 8

Synthesis of N-[3-(2-Chloro-4-fluoro-phenyl)-3-hydroxy-propyl]-sulfamide

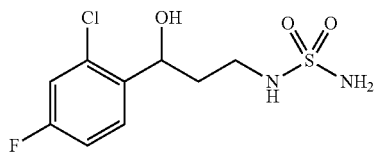

N-[3-(2-Chloro-4-fluoro-phenyl)-3-hydroxy-propyl]-sulfamide was prepared by the same procedure as example 7. ¹H NMR (DMSO-d₆) δ 7.57 (dd, J=8.7, 6.6 Hz, 1H), 7.35 (dd, J=8.8, 2.6 Hz, 1H), 7.26-7.18 (m, 1H), 6.46 (s, 2H), 6.40 (t, J=5.8 Hz, 1H), 5.38 (d, J=4.7 Hz, 1H), 4.93-4.86 (m, 1H), 3.05-2.90 (m, 2H), 1.89-1.79 (m, 2H). MS (ES⁺)=283 (MH)⁺.

Example 9

Synthesis of 3-(2-Fluoro-phenyl)-3-hydroxybutyl-1-sulfamide

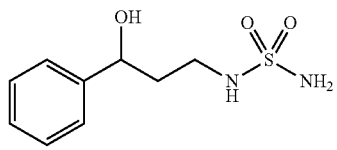 [SMILES: NS(=O)(=O)NCCC(O)c1ccccc1]

N-(3-phenyl-3-hydroxy-propyl)-sulfamide was prepared by the same procedure as example 6. ¹H NMR (DMSO-d₆) δ 7.38-7.29 (m, 4H), 7.30-7.21 (m, 1H), 6.48 (s, 2H), 6.40 (t, J=7.1 Hz, 1H), 5.21 (d, J=4.7 Hz, 1H), 4.65-4.58 (m, 1H), 3.00-2.90 (m, 2H), 1.82-1.73 (m, 2H). MS (ES⁺)=231 (MH)⁺.

Example 10

Synthesis of N-[3-(2-Fluoro-phenyl)-3-hydroxy-butyl]-sulfamide

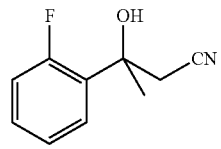

3-(2-Fluoro-phenyl)-3-hydroxy-butyronitrile was prepared by the same procedure of 3-(2-fluoro-phenyl)-3-hydroxy-propionitrile from 1-(2-fluoro-phenyl)-ethanone in example 6.

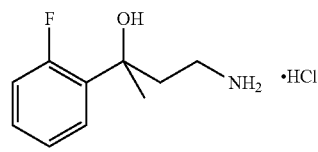

4-Amino-2-(2-fluoro-phenyl)-butan-2-ol hydrochloride.

To a stirring solution of 3-(2-fluoro-phenyl)-3-hydroxy-butyronitrile (878 mg, 4.9 mmol) in tetrahydrofuran (5 mL) was slowly added a solution of borane-tetrahydrofuran complex (12.8 mL, 12.8 mmol, 1M in tetrahydrofuran). After bubbling ceased, the reaction mixture was heated to 75° C. for 2 hours and then allowed to cool to ambient temperature and concentrated. Methanol (5 mL) was added dropwise followed by hydrogen chloride (5.4 mL, 23.8 mmol, 4N in 1,4-dioxane). The resulting mixture was heated to reflux for 2 hours, allowed to cool to ambient temperature and then concentrated at reduced pressure. The residue was triturated with ether and the precipitate was filtered, washed with ethyl acetate and air dried to give the product as a white solid (1 g, 92%).

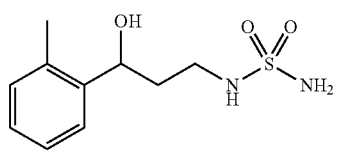 [SMILES: Cc1ccccc1C(O)CCNS(N)(=O)=O]

3-(2-Fluoro-phenyl)-3-hydroxybutyl-1-sulfamide. To a mixture of 4-amino-2-(2-fluoro-phenyl)-butan-2-ol hydrochloride (80 mg, 0.39 mmol) and sulfamide (75 mg, 0.79 mmol) in 1,4-dioxane (1.5 mL) was added triethylamine (0.11 mL, 0.79 mmol). The reaction mixture was heated at 110° C. for 24 hours, cooled to room temperature and partitioned between ethyl acetate (30 mL) and water (30 mL). The organic layer was dried (anhydrous magnesium sulfate), concentrated and purified by column chromatography through a silica gel cartridge (12 g) eluting with ethyl acetate/hexane (20% to 70%) to give the product as a white solid (27 mg, 26%). ¹H NMR (DMSO-d₆) δ 7.65-7.58 (m, 1H), 7.32-7.23 (m, 1H), 7.20-7.05 (m, 2H), 6.39 (s, 2H), 6.25 (t, J=7.1 Hz, 1H), 5.30 (s, 1H), 2.99-2.85 (m, 2H), 2.08-1.89 (m, 2H), 1.50 (s, 3H).

Example 11

Synthesis of 3-(2-Methyl-phenyl)-3-hydroxypropyl-1-sulfamide 3-(2-Methyl-phenyl)-3-hydroxypropyl-1-sulfamide was prepared by the same procedure as example 6. ¹H NMR (DMSO-d₆) δ 7.45-7.19 (m, 1H), 7.11-7.08 (m, 3H), 6.48 (s, 2H), 6.40 (t, J=7.1 Hz, 1H), 5.10 (d, J=4.7 Hz, 1H), 4.83-4.75 (m, 1H), 3.05-2.95 (m, 2H), 2.25 (s, 3H), 1.81-1.62 (m, 2H).

Example 12

Synthesis of 3-(2-Ethyl-phenyl)-3-hydroxypropyl-1-sulfamide

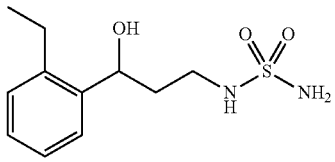 [SMILES: CCc1ccccc1C(O)CCNS(N)(=O)=O]

3-(2-Ethyl-phenyl)-3-hydroxypropyl-1-sulfamide was prepared by the same procedure as example 6. $^1$H NMR (DMSO-d$_6$) δ 7.45-7.39 (m, 1H), 7.10-7.08 (m, 3H), 6.45 (s, 2H), 6.40 (t, J=7.1 Hz, 1H), 5.09 (d, J=4.7 Hz, 1H), 4.88-4.79 (m, 1H), 3.06-2.88 (m, 2H), 2.70-2.50 (m, 2H), 1.79-1.65 (m, 2H), 1.12 (t, J=7.1 Hz, 3H).

Example 13

Synthesis of 3-(2-bromo-phenyl)-3-hydroxypropyl-1-sulfamide

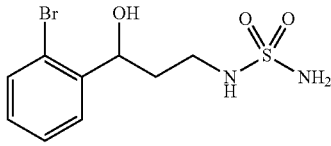 [SMILES: NS(=O)(=O)NCCC(O)c1ccccc1Br]

3-(2-bromo-phenyl)-3-hydroxypropyl-1-sulfamide was prepared by the same procedure as example 6. $^1$H NMR (DMSO-d$_6$) δ 7.58-7.51 (m, 2H), 7.41-7.32 (m, 1H), 7.20-7.13 (m, 1H), 6.45 (s, 2H), 6.35 (t, J=7.1 Hz, 1H), 5.48 (d, J=4.7 Hz, 1H), 4.89-4.80 (m, 1H), 3.05-2.88 (m, 2H), 1.92-1.76 (m, 1H), 1.72-1.59 (m, 1H).

Example 14

Synthesis of 3-(2-methoxy-phenyl)-3-hydroxypropyl-1-sulfamide

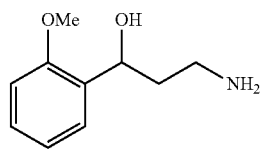 [SMILES: COc1ccccc1C(O)CCN]

3-Amino-1-(2-methoxy-phenyl)-propan-1-ol was prepared by the same procedure as 3-amino-1-(2-fluoro-phenyl)-propan-1-ol without adding methanol in the acidification step in example 6. $^1$H NMR (DMSO-d$_6$) δ 7.45-7.19 (m, 1H), 7.11-7.08 (m, 3H), 6.48 (s, 2H), 6.40 (t, J=7.1 Hz, 1H), 5.10 (d, J=4.7 Hz, 1H), 4.83-4.75 (m, 1H), 3.05-2.95 (m, 2H), 2.25 (s, 3H), 1.81-1.62 (m, 2H).

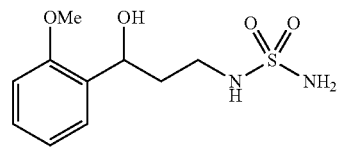 [SMILES: COc1ccccc1C(O)CCNS(N)(=O)=O]

3-(2-methoxy-phenyl)-3-hydroxypropyl-1-sulfamide was prepared by the same procedure as example 6. $^1$H NMR (DMSO-d$_6$) δ 7.41-7.31 (m, 1H), 7.21-7.13 (m, 1H), 6.98-6.88 (m, 2H), 6.42 (s, 2H), 6.28 (t, J=7.1 Hz, 1H), 5.02 (d, J=4.7 Hz, 1H), 4.93-4.85 (m, 1H), 3.75 (s, 3H), 3.02-2.83 (m, 2H), 1.83-1.28 (m, 2H).

Example 15

Synthesis of (S)-3-(2-Fluoro-phenyl)-3-hydroxypropyl-1-sulfamide

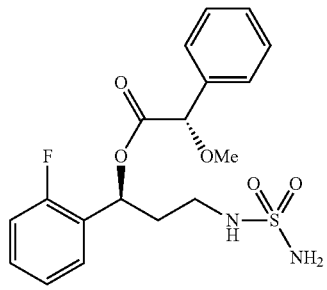 [SMILES: CO[C@H](C(=O)O[C@@H](CCNS(N)(=O)=O)c1ccccc1F)c1ccccc1]

(S)-Methoxy-phenyl-acetic acid 3-sulfamide-(S)-1-(2-fluoro-phenyl)-propyl ester

To a solution of N-[3-(2-fluoro-phenyl)-3-hydroxy-propyl]-sulfamide (1.8 g, 7.32 mmol), (S)-methoxy-phenyl-acetic acid (1.58 g, 9.51 mmol) in dichloromethane (20 mL) was added 1-ethyl-3-(3-dimethylaminopropyl) carbodiimide) (2.1 g, 11 mmol) and N,N-dimethylaminopyridine (89 mg, 0.73 mmol). The reaction mixture was stirred for 18 hours, diluted with dichloromethane (30 mL) and washed with water. The organic layer was dried (anhydrous magnesium sulfate), concentrated and purified by column chromatography through a silica gel cartridge (120 g) eluting with ethyl acetate/toluene (0% to 20%) to give the two diasteromers (S)-methoxy-phenyl-acetic acid 3-sulfamide-(R)-1-(2-fluoro-phenyl)-propyl ester, higher Rf compound (1.1 g, 38%, colorless oil); (S)-methoxy-phenyl-acetic acid 3-sulfamide-(S)-1-(2-fluoro-phenyl)-propyl ester, lower Rf compound (1.6 g, 55%, colorless oil). $^1$H NMR (CDCl$_3$) δ 7.40-7.31 (m, 5H), 7.21-7.12 (m, 1H), 6.96-6.78 (m, 3H), 6.17 (dd, J=11.0, 7.2 Hz, 1H), 5.10-4.98 (br s, 1H), 4.90-4.78 (br s, 2H), 4.88 (s, 1H), 3.38 (s, 3H), 3.21-3.10 (m, 2H), 2.20-2.02 (m, 2H).

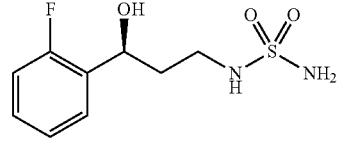 [SMILES: NS(=O)(=O)NCC[C@H](O)c1ccccc1F]

(S)-3-(2-Fluoro-phenyl)-3-hydroxypropyl-1-sulfamide.

To a solution of (S)-Methoxy-phenyl-acetic acid 3-sulfamide-(S)-1-(2-fluoro-phenyl)-propyl ester (1.5 g, 3.8 mmol) in tetrahydrofuran (20 mL) at 0° C. was added lithium hydroxide (4.2 mL, 4.2 mmol, 1 N in water). The cooling bath was removed and the reaction mixture was stirred at room temperature for 1 hour. Additional lithium hydroxide (0.76 mL, 0.76 mmol, 1 N in water) was added the reaction mixture was stirred for 1 hour. Ethyl acetate (30 mL) was added and the solution was washed with water (20 mL), dried (anhydrous magnesium sulfate), concentrated and purified through column chromatography through a silica gel cartridge (40 g) eluting with ethyl acetate/hexane (20% to 70%) to give the product as a colorless oil that crystallized on standing (740 mg, 78%). $^1$H NMR (DMSO-$d_6$) δ 7.53-7.48 (m, 1H), 7.32-7.08 (m, 3H), 6.48 (s, 2H), 6.41 (t, J=7.1 Hz, 1H), 5.38 (d, J=4.7 Hz, 1H), 4.93-4.86 (m, 1H), 3.05-2.89 (m, 2H), 1.88-1.76 (m, 2H). MS (ES$^+$)=249 (MH)$^+$.

Example 16

Synthesis of (R)-3-(2-Fluoro-phenyl)-3-hydroxypropyl-1-sulfamide

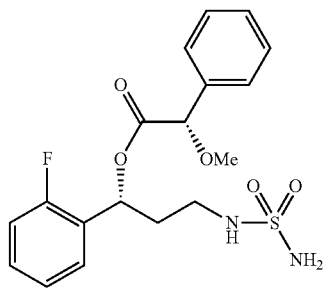 [SMILES: CO[C@H](C(=O)O[C@H](CCNS(N)(=O)=O)c1ccccc1F)c1ccccc1]

(S)-Methoxy-phenyl-acetic acid 3-sulfamide-(R)-1-(2-fluoro-phenyl)-propyl ester was prepared by the same procedure as example 16. $^1$H NMR (CDCl$_3$) δ 7.50-7.42 (m, 2H), 7.42-7.30 (m, 3H), 7.30-7.16 (m, 2H), 7.09-6.98 (m, 2H), 6.15 (dd, J=11.2, 7.1 Hz, 1H), 5.00-4.85 (br s, 1H), 4.71 (s, 1H), 4.63-4.50 (br s, 2H), 3.40 (s, 3H), 3.05-2.85 (m, 2H), 2.15-2.02 (m, 2H).

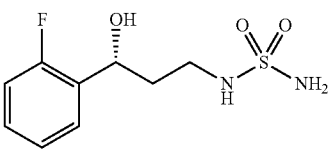

(R)-3-(2-Fluoro-phenyl)-3-hydroxypropyl-1-sulfamide.

To a solution of (S)-Methoxy-phenyl-acetic acid 3-sulfamide-(R)-1-(2-fluoro-phenyl)-propyl ester (43 mg, 0.11 mmol) in tetrahydrofuran (1 mL) was added lithium hydroxide (0.16 mL, 0.16 mmol, 1 N in water). The reaction mixture was stirred at room temperature for 1 hour. Ethyl acetate (30 mL) was added and the solution was washed with water (10 mL), dried (anhydrous magnesium sulfate), concentrated and purified through column chromatography through a silica gel cartridge (12 g) eluting with ethyl acetate/hexane (20% to 70%) to give the product as a white solid (19 mg, 70%). $^1$H NMR (DMSO-$d_6$) δ 7.53-7.48 (m, 1H), 7.35-7.08 (m, 3H), 6.48 (s, 2H), 6.41 (t, J=7.1 Hz, 1H), 5.38 (d, J=4.7 Hz, 1H), 4.93-4.86 (m, 1H), 3.05-2.91 (m, 2H), 1.88-1.78 (m, 2H). MS (ES$^+$)=249 (MH)$^+$.

Example 17

Synthesis of (R)—N-[3-(2-Chloro-phenyl)-3-hydroxy-propyl]-sulfamide

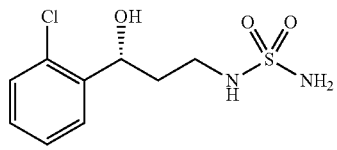

(R)-3-(2-Chloro-phenyl)-3-hydroxypropyl-1-sulfamide was prepared by the same procedure as example 16. $^1$H NMR (DMSO-$d_6$) δ 7.61-7.55 (m, 1H), 7.40-7.33 (m, 2H), 7.32-7.21 (m, 1H), 6.50 (s, 2H), 6.40 (t, J=7.1 Hz, 1H), 5.45 (d, J=4.7 Hz, 1H), 4.99-4.89 (m, 1H), 3.13-2.92 (m, 2H), 1.92-1.80 (m, 1H) 1.76-1.62 (m, 1H). MS (ES$^+$)=265 (MH)$^+$.

Example 18

Synthesis of (S)-3-(2-Chloro-phenyl)-3-hydroxypropyl-1-sulfamide

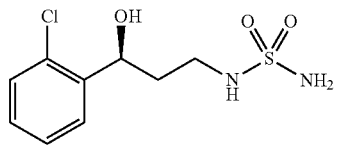 [SMILES: NS(=O)(=O)NCC[C@H](O)c1ccccc1Cl]

(S)-3-(2-Chloro-phenyl)-3-hydroxypropyl-1-sulfamide was prepared by the same procedure as example 16. $^1$H NMR (DMSO-$d_6$) δ 7.60-7.58 (m, 1H), 7.40-7.33 (m, 2H), 7.30-7.21 (m, 1H), 6.48 (s, 2H), 6.40 (t, J=7.1 Hz, 1H), 5.45 (d, J=4.7 Hz, 1H), 4.98-4.90 (m, 1H), 3.10-2.95 (m, 2H), 1.83-1.79 (m, 1H), 1.78-1.63 (m, 1H). MS (ES$^+$)=265 (MH)$^+$.

Examples 19 provides methods for preparing representative compounds of formula (II). The skilled practitioner will know how to substitute the appropriate reagents, starting materials and purification methods known to those skilled in the art, in order to prepare additional compounds of the present invention.

Example 19

Synthesis of 4-(2-Fluorophenyl)-4-hydroxypiperidine-1-sulfonamide

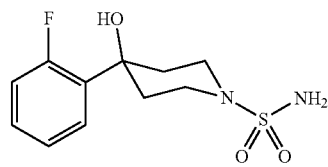 [SMILES: NS(=O)(=O)N1CCC(O)(c2ccccc2F)CC1]

4-(2-Fluoro-phenyl)-4-hydroxypiperidine-1-carboxylic acid tert-butyl ester.

To a stirring solution of 1-bromo-2-fluorobenzene (2 g, 11.4 mmol) in tetrahydrofuran (30 mL) at −70° C. under nitrogen was added a solution of n-butyllithium (5.0 mL, 12.6 mmol, 2.5 M in hexane). After 30 minutes, 4-oxo-piperidine-1-carboxylic acid tert-butyl ester (2.97 g, 14.9 mmol) was added in one portion. After 30 minutes, the reaction was quenched with water (2 mL) and was allowed to warm to ambient temperature. After one hour at ambient temperature, the reaction mixture was poured into water (75 mL) and the mixture was extracted with ethyl acetate (2×75 mL). The organic layers were combined, washed with saturated aqueous sodium chloride and concentrated at reduced pressure. The resulting crude product was triturated with hexane (35 mL) for 2 hours, filtered and dried to give the product as a white solid (2.22 g, 65%). $^1$H NMR (CDCl$_3$) δ 7.45 (m, 1H,), 7.24 (m, 1H), 7.19-7.01 (m, 2H), 4.03 (br s, 2H), 3.23 (m, 2H), 18 (m, 3H), 1.81 (m, 2H), 1.45 (m, 9H). MS (ES$^+$)=296 (MH)$^+$.

4-(2-Fluorophenyl)-4-hydroxypiperidine-1-sulfonamide.

To a stirring solution of 4-(2-fluoro-phenyl)-4-hydroxy-piperidine-1-carboxylic acid tert-butyl ester (1.2 g, 4.06 mmol) in ethyl acetate (5 mL) was added hydrogen chloride (15 mL, 4N in 1,4-dioxane) and the resulting solution was stirred for 3 hours during which time a precipitate formed. The reaction mixture was concentrated at reduced pressure to give the crude product, 4-(2-fluoro-phenyl)-piperidin-4-ol hydrochloride, which was used in the next step without purification. To a solution of chlorosulfonyl isocyanate (0.35 mL, 4.06 mmol) in dichloromethane (10 mL) at 3° C. was added tert-butanol (0.39 mL, 4.06 mmol). After 25 minutes, pyridine (0.72 mL, 8.9 mmol) was added and the resulting mixture was stirred for 40 minutes during which time a precipitate formed. This slurry was added via pipette to a solution of crude 4-(2-fluoro-phenyl)-piperidin-4-ol hydrochloride (940 mg, 4.06 mmol) and triethylamine (0.62 mL, 4.47 mmol) in dichloromethane (6 mL) at 3° C. The resulting mixture was allowed to warm to ambient temperature over 4 hours. The reaction mixture was diluted with dichloromethane (100 mL) and washed with dilute hydrochloric acid (40 mL, 0.1N) followed by saturated aqueous sodium chloride (30 mL). The organic layer was concentrated at reduce pressure. The resulting oil was dissolved in ethyl acetate (5 mL) and to this solution was added hydrogen chloride (15 mL, 4N in 1,4-dioxane) and the resulting solution was stirred for 5 hours. The reaction mixture was concentrated at reduced pressure and the resulting solid was purified by column chromatography through a silica gel cartridge (12 g) eluting with ethyl acetate/hexane (1:9 to 2:5) to give the product as a white solid (420 mg, 38% over 3 steps). $^1$H NMR (DMSO-d$_6$) δ 7.65 (m, 1H,), 7.30 (m, 1H), 7.24-7.09 (m, 2H), 6.75 (s, 2H), 5.28 (s, 1H), 3.31 (m, 2H), 2.92 (m, 2H), 2.22 (m, 2H), 1.68 (m, 2H). MS (ES$^+$)=275 (MH)$^+$.

Example 20

Synthesis of 3-(2-Trifluoromethyl-phenyl)-3-hydroxypropyl-1-sulfamide

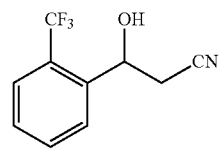 [SMILES: N#CCC(O)c1ccccc1C(F)(F)F]

3-Hydroxy-3-(2-trifluoromethyl-phenyl)-propionitrile was prepared by the same procedure of 3-(2,4-difluoro-phenyl)-3-hydroxy-propionitrile in example 4.

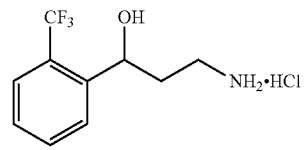

3-Amino-1-(2-trifluoromethyl-phenyl)-propan-1-ol hydrochloride salt was prepared by the same procedure of 3-Amino-1-(2,4-difluoro-phenyl)-propan-1-ol hydrochloride salt in example 4.

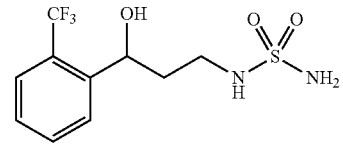 [SMILES: NS(=O)(=O)NCCC(O)c1ccccc1C(F)(F)F]

3-(2-Trifluoromethyl-phenyl)-3-hydroxypropyl-1-sulfamide was prepared by the same procedure of 3-(2,4-difluoro-phenyl)-3-hydroxypropyl-1-sulfamide in example 4. $^1$H NMR (DMSO-d$_6$) δ 7.80 (d, J=7.4 Hz, 1H), 7.73-7.65 (m, 2H), 7.50-7.47 (m, 1H), 6.48 (s, 2H), 6.41 (t, J=7.1 Hz, 1H), 5.55 (d, J=4.7 Hz, 1H), 4.92-4.82 (m, 1H), 3.15-3.02 (m, 1H), 2.98-2.85 (m, 1H), 1.89-1.69 (m, 2H). MS (ES$^+$)=299 (MH)$^+$.

Example 21

Synthesis of 3-(2-Nitro-phenyl)-3-hydroxypropyl-1-sulfamide

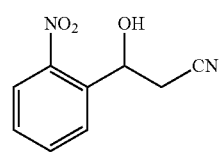 [SMILES: N#CCC(O)c1ccccc1[N+](=O)[O-]]

3-Hydroxy-3-(2-nitro-phenyl)-propionitrile was prepared by the same procedure of 3-(2-fluoro-phenyl)-3-hydroxy-propionitrile in example 6.

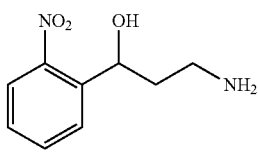 [SMILES: NCCC(O)c1ccccc1[N+](=O)[O-]]

3-Amino-1-(2-nitro-phenyl)-propan-1-ol was prepared by the same procedure of 3-amino-1-(2-fluoro-phenyl)-propan-1-ol in example 6.

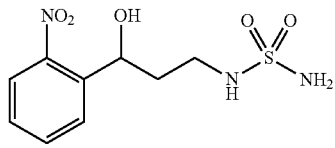 [SMILES: NS(=O)(=O)NCCC(O)c1ccccc1[N+](=O)[O-]]

3-(2-Nitro-phenyl)-3-hydroxypropyl-1-sulfamide was prepared by the same procedure of 3-(2-fluoro-phenyl)-3-hydroxypropyl-1-sulfamide in example 6. $^1$H NMR (DMSO-$d_6$) δ 7.89 (d, J=8.6 Hz, 1H), 7.81-7.71 (m, 2H), 7.55-7.48 (m, 1H), 6.50 (s, 2H), 6.43 (t, J=7.1 Hz, 1H), 5.68 (d, J=4.4 Hz, 1H), 5.07-5.01 (m, 1H), 3.12-2.88 (m, 2H), 1.92-1.69 (m, 2H). MS (ES$^+$)=276 (MH)$^+$.

Example 22

Synthesis of 3-(2,6-Difluoro-phenyl)-3-hydroxypropyl-1-sulfamide 3-(2,6-Difluoro-phenyl)-3-hydroxy-propionitrile was prepared by the same procedure of 3-(2-fluoro-phenyl)-3-hydroxy-propionitrile in example 6.

3-Amino-1-(2,6-difluoro-phenyl)-propan-1-ol was prepared by the same procedure of 3-amino-1-(2-fluoro-phenyl)-propan-1-ol in example 6.

3-(2,6-Difluoro-phenyl)-3-hydroxypropyl-1-sulfamide was prepared by the same procedure of 3-(2-fluoro-phenyl)-3-hydroxypropyl-1-sulfamide in example 6. $^1$H NMR (DMSO-$d_6$) δ 7.36-7.27 (m, 1H), 7.02 (t, J=8.6 Hz, 2H), 6.46-6.40 (m, 3H), 5.41 (d, J=4.7 Hz, 1H), 4.99-4.91 (m, 1H), 3.02-2.81 (m, 2H), 2.19-2.05 (m, 1H), 1.90-1.81 (m, 1H). MS (ES$^+$)=267 (MH)$^+$.

Example 23

Synthesis of 3-(2-Phenyl-phenyl)-3-hydroxypropyl-1-sulfamide 3-(2-Phenyl-phenyl)-3-hydroxypropyl-1-sulfamide.

A mixture of Example 13, 3-(2-bromo-phenyl)-3-hydroxypropyl-1-sulfamide (30 mg, 0.096 mmol), phenylboronic acid (20 mg, 0.16 mmol), 1,1'-bis(diphenylphosphino)ferrocene-palladium(II)dichloride dichloromethane complex (7 mg, 0.01 mmol) and potassium carbonate (20 mg, 0.14 mmol) in 1,4-dioxane (0.8 mL) and water (0.8 mL) was heated at 86° C. for 4 h. After cooling down, the reaction mixture was partitioned between water and ethyl acetate, the organic layer was dried (sodium sulfate), filtered, concentrated and purified through preparative thin layer chromatography (1 mm) eluting with 50% ethyl acetate/hexanes to give 17 mg (57%) of the product as a white solid. $^1$H NMR (CD$_3$OD) δ 7.63 (d, J=8.9 Hz, 1H), 7.45-7.26 (m, 7H), 7.17 (d, J=7.6 Hz, 1H), 4.86-4.81 (m, 1H), 3.04-2.89 (m, 2H), 1.94-1.28 (m, 2H). MS (ES$^+$)=307 (MH)$^+$.

Example 24

Synthesis of 3-[2-(5-Chloro-pyridine-3-yl)-phenyl]-3-hydroxypropyl-1-sulfamide

3-[2-(5-Chloro-pyridine-3-yl)-phenyl]-3-hydroxypropyl-1-sulfamide was prepared by the same procedure as example 23. $^1$H NMR (CD$_3$OD) δ 8.57 (s, 1H), 8.47 (s, 1H), 7.90 (s, 1H), 7.68 (d, J=7.3 Hz, 1H), 7.49 (t, J=7.5 Hz, 1H), 7.41-7.35 (m, 1H), 7.22 (d, J=7.6 Hz, 1H), 4.75-4.70 (m, 1H), 3.02-2.93 (m, 2H), 2.01-1.81 (m, 2H). MS (ES$^+$)=342 (MH)$^+$.

Formulations

The present invention also relates to compositions or formulations which comprise the neuroprotective agents according to the present invention. In general, the compositions of the present invention comprise an effective amount of one or more hydroxylated sulfamides and salts thereof according to the present invention which are effective for providing neuroprotection; and one or more excipients.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known neuroprotective agents. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more hydroxylated sulfamides according to the present invention and one or more excipients; from about 0.01 mg to about 100 mg of one or more hydroxylated sulfamides according to the present invention and one or more excipients;

and from about 0.1 mg to about 10 mg of one or more hydroxylated sulfamides according to the present invention; and one or more excipients.

Procedures

The following procedures can be utilized in evaluating and selecting compounds as neuroprotective agents.

Cell cultures: All compounds are screened with dissociated hippocampal cultures derived from embryonic day 18 rats as the primary test system. With this preparation, primary neurons are used to test for toxicity as well as neuroprotection in a highly relevant experimental system to epilepsy. In brief, hippocampal tissue are obtained commercially through Brain Bits (Springfield, Ill.) and cultures prepared as previously described by Brewer (Brewer, G. J. Serum-free B27/neurobasal medium supports differentiated growth of neurons from the striatum, substantia nigra, septum, cerebral cortex, cerebellum and dentate gyms, J. Neurosci. Res. 1995, 42, 674-683.). The hippocampal neurons are platted at low density (10,000 cell/well) in a 96-well format and maintained in serum-free medium consisting of Neurobasal Medium supplemented with B27 and GlutaMAX (Gibco). Pre-coated poly-L-lysine coated plates are used because of the preferential adherence and survival of hippocampal neurons on this matrix support.

In Vitro Toxicity Testing:

Carboxyfluorescein (CFDA) was used a vital stain for all cell toxicity and neuroprotection studies. With the use of the CytoFluor fluorimeter, the CFDA assay was employed to assess the viability of neurons. CFDA is a dye that becomes fluorescent upon cell entry and cleavage by cytosolic esterases (Petroski, R. E.; Geller, H. M Selective labeling of embryonic neurons cultures on astrocyte monolayers with 5(6)-carboxyfluorescein diacetate (CFDA). J. Neurosci. Methods 1994, 52, 23-32.). Neuronal specificity is obtained relative to astrocytes because the cleaved dye is extruded extracellularlly by glia with time, while dye in neurons remains intracellular. Previous experience with this assay showed a good correlation with neuronal cell counts stained immunocytochemically with neuron specific enolase antibodies, a reference marker for neuronal identity in complex cultures. To further asses the culture responses, a propidium iodide method was used as previously described (Sarafian, T. A.; Kouyoumjian, S.; Tashkin, D.; Roth, M. D. Synergistic cytotoxicity of 9-tetrahydrocannabianol and butylated hydroxyanisole, Tox. Letters, 2002. 133, 171-179.) to measure the number of dead cells. Propidium iodide becomes fluorescent when binding to the DNA of dead cells. Cultures were treated on day 2 with the test agent and then the two assays were conducted after a four day test period. For all assays, a 96-well format was used. For the screen, log concentration-effect studies were conducted from 10 nM to 1 mM with 8 replications. The duration of the test period was five days. Cultures were given a complete change of medium prior to the initiation of the treatment period.

Experimental details for the propidium iodide assay (Sarafian, T. A.; Kouyoumjian, S.; Tashkin, D.; Roth, M. D. Synergistic cytotoxicity of 9-tetrahydrocannabianol and butylated hydroxyanisole, Tox. Letters, 2002. 133, 171-179.): All test compounds were dissolved to 10 mM in Dulbecco's phosphate buffered saline (DPBS; Sigma:D-5780) prior to testing. On day two after plating, the test compound was added to the hippocampal cultures for a 4 day test period. Compounds were tested from 1 nM to 1 mM. At the conclusion of the test period, the cultures were tested for the amount of cell death by the propidium iodide method. Propidium iodide (PI) stock solution of 1 mg/ml (1.5 mM) was obtained from Sigma. The PI stock was diluted 1:30 in DPBS for a final working concentration of 50 µM. After removal of the growth medium, 50 µl of the 50 µM PI solution was added to cultures and allowed to incubate in the dark at room temperature for 15 min. The cultures were then assessed for fluorescence intensity at Ex536/Em590 nm in a CytoFluor fluorimeter. Results were expressed in relative fluorescent units and as a % of control values.

Experimental details for the CFDA assay (Petroski, R. E.; Geller, H. M Selective labeling of embryonic neurons cultures on astrocyte monolayers with 5(6)-carboxyfluorescein diacetate (CFDA). J. Neurosci. Methods 1994, 52, 23-32.): All test compounds were dissolved to 10 mM in Dulbecco's phosphate buffered saline (DPBS; Sigma:D-5780) prior to testing. On day two after plating, the test compound was added to the hippocampal cultures for a 4 day test period. Compounds were tested from 1 nM to 1 mM. At the conclusion of the test period, the cultures were tested for the amount of neuronal viability by the CFDA method. For the neuronal viability assay, 1 mg of 5,6-carboxyfluorescein diacetate (CFDA) dye (Sigma) was dissolved in 100 ml of DPBS (Gibco:D-5780) and kept in the dark until added to the hippocampal cultures. After a complete change of medium of day 5 hippocampal test cultures, 100 µl CFDA dye solution was added for 15 min of incubation at 37° C. in the dark. At the conclusion of the incubation period, the dye was removed from the cultures and washed once with 100 µl of DPBS. After removal of the first wash, a second wash of DPBS was added to the culture and then incubated for 30 min to allow the efflux of dye out of glia in the cultures. At the conclusion of the 30 min efflux period, the culture efflux medium was removed and 100 µl of 0.1% triton-X100 in water was added to the cultures before reading at Ex490/Em517 in a CytoFluor fluorimeter. Results were expressed in relative fluorescent units (RFU).

Neuroprotection Assays:

Potent neuroprotection is the distinguishing characteristic that separates this program's anticonvulsants from all other commercial drugs for epilepsy. The experimental details and the rationale for the implemented assays are essential in differentiating these compounds from that of others. The central objective of all neuroprotective assays was their relevancy to excitotoxicity and oxidative stress related to epilepsy. Both the amount of glutamate and hydrogen peroxide used in the assays, as well as the time of treatment and duration of the experiment, were designed to be relevant to epilepsy. Further, all time parameters employed in these studies were empirically determined to be within the limits of reversible toxic events, yet using amounts of glutamate and hydrogen peroxide that were relevant to the disease. In regard to glutamate toxicity, a critical feature was the duration of treatment of the hippocampal neurons. The rational for using a short 5 min treatment with glutamate was based on the observation of Randall and Thayer (Randall, R. D.; Thayer, S. A. Glutamate-induced calcium transient triggers calcium overload and neurotoxicity in rat hippocampal neurons, J. Neurosci. 1992, 12, 1882-1895). Their study demonstrated that a short-term treatment with glutamate produced a delayed but substantial increase in intracellular calcium that overloaded the neuron and produced cell death. The rationale is that this intense burst of glutamate and resulting calcium overload is relevant to seizures and therefore was important data to capture in the screening assay. The amount of glutamate (30 µM) employed in our screening was based on the basal levels of glutamate observed in microdialysis measurements of hippocampus from epileptogenic patients (Cavus et al. Decreased hippocampal volume on MRI is associated with increased extracellular glutamate in epilepsy patients, *Epilepsia,* 2008, 49, 1358-1366.). In regard to hydrogen peroxide, the amount employed (10 µM) was detected in the hippocampus of rats after kainate-induced status epilepticus (Jarrett et. al., Mitochondrial DNA damage and impaired base excision repair during epileptogenesis, *Neurobiol. Dis.* 2008, 30, 130-138). To produce neural damage and death with these amounts of glutamate and hydrogen peroxide, the cultures were changed to a medium with significant depletion of antioxidant components in the defined medium supplement B-27 just prior to treatment with the compounds. This was performed to obtain a significant and reproducible toxic signal in the hippocampal neurons and because loss of antioxidant control may be a component of epileptogenesis (Waldbaum and Patel, Mitochondria, oxidative stress and temporal lobe epilepsy, *Epilepsy Res.* 2010 88, 23-45.; Wu et al., Mitochondrial DNA mutation-elicited oxidative stress, oxidative damage, and altered gene expression in cultured cells of patients with MERRF syndrome, *Mol. Neurobiol.* 2010, 41, 256-266.). Neuroprotection studies with hydrogen peroxide were conducted with cultures that were between day 12 and day 18. Studies of neuroprotection glutamate were conducted between day 19 and day 22. Assays for neuronal viability and cell death were identical to those described in the cell toxicity section.

Experimental Details of the Propidium Iodide Neuroprotection Assay:

Neuroprotection from oxidative stress: All test compounds are dissolved to 10 mM in Dulbecco's phosphate buffered saline (DPBS; Sigma:D-5780) prior to testing. To test for neuroprotection from hydrogen peroxide, day 11 hippocampal cultures are given a complete change of medium containing 100 µl of Neurobasal medium with B27 that contains no antioxidants. Twenty four hours after the change in medium, the hydrogen peroxide neuroprotection studies are started. The test compound is added to the hippocampal cultures for a 4 hour test period in concentrations that ranged from 1 nM to 300 µM. Concurrent with the treatment of test compound, 10 µM hydrogen peroxide is added for the 4 hour test period. At the conclusion of the test period, the cultures are tested for the amount of cell death by the propidium iodide method. Propidium iodide (PI) stock solution of 1 mg/ml (1.5 mM) is obtained from Sigma. The PI stock is diluted 1:30 in DPBS for a final working concentration of 50 µM. After removal of the growth medium, 50 µl of the 50 µM PI solution is added to cultures and allowed to incubate in the dark at room temperature for 15 min. The cultures are then assessed for fluorescence intensity at Ex536/Em590 nm in a CytoFluor fluorimeter. Results are expressed in relative fluorescent units and $EC_{50}$'s calculated from the dose response of the test compound.

Neuroprotection from Excitotoxicity:

For the glutamate neuroprotection studies with the propidium iodide assay, several modifications are made from the method described for the hydrogen peroxide assay. For the glutamate neuroprotection assay, day 19 hippocampal cultures are given a complete change of medium containing 100 µl of Neurobasal medium with B27 that contained no antioxidants. Twenty four hours after the change in medium, the glutamate neuroprotection studies are started. The day 20 cultures are treated for 5 min with 30 µM glutamate dissolved in DPBS. For this treatment, a 900 µM solution of glutamate is prepared and then 3.3 µL of this solution is added to the culture well containing 100 µL of media. After this short treatment, the medium containing the glutamate is removed from the cultures and fresh medium with antioxidants added. The test compound is then added to the hippocampal cultures for a 4 hour test period in concentrations that ranged from 1 nM to 300 µM. At the conclusion of the test period, the cultures are tested for the amount of cell death by the propidium iodide method. Propidium iodide (PI) stock solution of 1 mg/ml (1.5 mM) is obtained from Sigma. The PI stock is diluted 1:30 in DPBS for a final working concentration of 50 µM. After removal of the growth medium, 50 µl of the 50 µM PI solution is added to cultures and allowed to incubate in the dark at room temperature for 15 min. The cultures are then assessed for fluorescence intensity at Ex536/Em590 nm in a CytoFluor fluorimeter. Results are expressed in relative fluorescent units and $EC_{50}$'s calculated from the dose response of the test compound.

Experimental Details of the CFDA Neuroprotection Assay:

Neuroprotection from Oxidative Stress:

All test compounds are dissolved to 10 mM in Dulbecco's phosphate buffered saline (DPBS; Sigma:D-5780) prior to testing. To test for neuroprotection from hydrogen peroxide, day 11 hippocampal cultures are given a complete change of medium containing 100 µl of Neurobasal medium with B27 that contained no antioxidants. Twenty four hours after the change in medium, the hydrogen peroxide neuroprotection studies are started. The test compound is added to the day 12 hippocampal cultures for a 4 hour test period in concentrations that ranged from 1 nM to 300 µM. Concurrent with the treatment of test compound, 10 µM hydrogen peroxide is added for the 4 hour test period. At the conclusion of the test period, the cultures are tested for the amount of neuronal viability by the CFDA method. For the neuronal viability assay, 1 mg of 5,6-carboxyfluorescein diacetate (CFDA) dye (Sigma) is dissolved in 100 ml of DPBS (Gibco:D-5780) and kept in the dark until added to the hippocampal cultures. After a complete change of medium of day 12 hippocampal test cultures, 100 µl CFDA dye solution is added for 15 min of incubation at 37° C. in the dark. At the conclusion of the incubation period, the dye is removed from the cultures and washed once with 100 µl of DPBS. After removal of the first wash, a second wash of DPBS is added to the culture and then incubated for 30 min to allow the efflux of dye out of glia in the cultures. At the conclusion of the 30 min efflux period, the culture efflux medium is removed and 100 µl of 0.1% triton-X100 in water is added to the cultures before reading at Ex490/Em517 in a CytoFluor fluorimeter. Results are expressed in relative fluorescent units (RFU) and $EC_{50}$'s calculated from the dose response of the test compound.

Neuroprotection from Excitotoxicity:

For the glutamate neuroprotection studies with the CFDA assay, several modifications are made from the method described for the hydrogen peroxide assay. For the glutamate neuroprotection assay, day 19 hippocampal cultures are given a complete change of medium containing 100 µl of Neurobasal medium with B27 that contained no antioxidants. Twenty four hours after the change in medium, the glutamate neuroprotection studies are started. The day 20 cultures are treated for 5 min with 30 µM glutamate dissolved in DPBS. For this treatment, a 900 µM solution of glutamate is prepared and then 3.3 µL of this solution is added to the culture well containing 100 µL of media. After this short treatment, the medium containing the glutamate is removed from the cultures and fresh medium with antioxidants added. The test compound is then added to the hippocampal cultures for a 4 hour test period in concentrations that ranged from 1 nM to 300 µM At the conclusion of the test period, the cultures are tested for the amount of neuronal viability by the CFDA method. For the neuronal viability assay, 1 mg of 5,6-carboxyfluorescein diacetate (CFDA) dye (Sigma) is dissolved in 100 ml of DPBS (Gibco:D-5780) and kept in the dark until added to the hippocampal cultures. After a complete change of medium of day 20 hippocampal test cultures, 100 µl CFDA dye solution is added for 15 min of incubation at 37° C. in the dark. At the conclusion of the incubation period, the dye is removed from the cultures and washed once with 100 µl of DPBS. After removal of the first wash, a second wash of DPBS is added to the culture and then incubated for 30 min to allow the efflux of dye out of glia in the cultures. At the conclusion of the 30 min efflux period, the culture efflux medium is removed and 100 µl of 0.1% triton-X100 in water is added to the cultures before reading at Ex490/Em517 in a CytoFluor fluorimeter. Results are expressed in relative fluorescent units (RFU) and $EC_{50}$'s calculated from the dose response of the test compound. Results are expressed in relative fluorescent units and $EC_{50}$'s calculated from the dose response of the test compound.

Seizure-related assays, Maximal electroshock test: The most definitive assay for antiseizure activity is the maximal electroshock (MES) test (Swinyard, E. A. Laboratory evaluation of antiepileptic drugs: review of laboratory methods, *Epilepsia*, 1969, 10, 107-119.). This model, which is highly predictive of efficacy in human epilepsy, is utilized to demonstrate antiseizure activity in mice after i.p. administration and in rats after oral administration. With both rodent assays, the duration of action is of high importance as well as the potency of the response.

Results for representative compounds according to the present invention are listed in Table 3 below.

TABLE 3

Examples of Propyl Hydroxylated Sulfamide Compounds and their Potencies for Biological Activity

| Example number | Structures | NP* from Glutamate PI | NP* from Glutamate CFDA | NP** from HP PI | NP** from HP CFDA | MES*** Duration |
|---|---|---|---|---|---|---|
| | | | EC50 | | | |
| 1 | 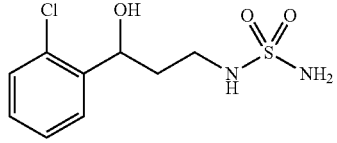 | 100 nM | 100 nM | 1 µM | 30 µM | 2 hr |
| 2 | 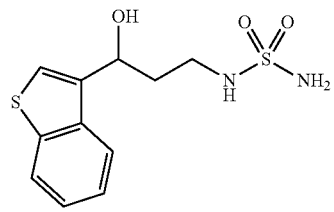 [SMILES: NS(=O)(=O)NCCC(O)c1csc2ccccc12] | 3 µM | 100 µM | 30 µM | 3 µM | — |
| 3 | 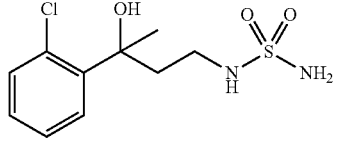 | >300 µM | >300 µM | >300 µM | 300 µM | — |
| 4 | 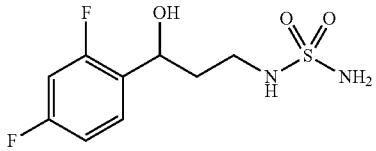 [SMILES: NS(=O)(=O)NCCC(O)c1ccc(F)cc1F] | Not done | Not done | Not done | Not done | — |
| 5 | 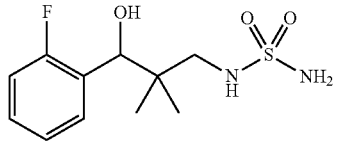 [SMILES: CC(C)(CNS(N)(=O)=O)C(O)c1ccccc1F] | 100 nM | 100 nM | >300 µM | >300 µM | — |
| 6 | 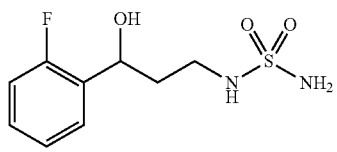 | 100 nM | 1 µM | 10 nM | 10 nM | 4 hr at 100 mg/kg |

TABLE 3-continued

Examples of Propyl Hydroxylated Sulfamide Compounds and their Potencies for Biological Activity

| Example number | Structures | NP* from Glutamate PI | NP* from Glutamate CFDA | NP** from HP PI | NP** from HP CFDA | MES*** Duration |
|---|---|---|---|---|---|---|
| | | | EC50 | | | |
| 7 | [structure: 2,5-difluorophenyl propyl hydroxyl sulfamide] | 3 µM | 30 µM | 1 nM | 10 nM | — |
| 8 | [structure: 2-chloro-4-fluorophenyl propyl hydroxyl sulfamide] | 10 µM | >300 µM | >300 µM | >300 µM | — |
| 9 | [structure: phenyl propyl hydroxyl sulfamide] | >300 µM | 300 µM | >300 µM | >300 µM | — |
| 10 | [structure: 2-fluorophenyl methyl propyl hydroxyl sulfamide] | 10 µM | 10 µM | 300 µM | 100 nM | — |
| 11 | [structure: 2-methylphenyl propyl hydroxyl sulfamide] | >300 µM | >300 µM | Not done | Not done | — |
| 12 | [structure: 2-ethylphenyl propyl hydroxyl sulfamide] | 10 µM | 10 nM | 10 nM | >300 µM | — |
| 13 | [structure: 2-bromophenyl propyl hydroxyl sulfamide] | 100 µM | 10 nM | 10 nM | 300 µM | — |
| 14 | [structure: 2-methoxyphenyl propyl hydroxyl sulfamide] | 100 nM | 10 nM | 10 nM | 10 µM | — |
| 15 | [structure: (S)-2-fluorophenyl propyl hydroxyl sulfamide] | 10 nM | 10 nM | 1 nM | 1 nM | 4 hrs at 100 mg/kg |

TABLE 3-continued

Examples of Propyl Hydroxylated Sulfamide Compounds and their Potencies for Biological Activity

| Example number | Structures | NP* from Glutamate PI | NP* from Glutamate CFDA (EC50) | NP** from HP PI | NP** from HP CFDA | MES*** Duration |
|---|---|---|---|---|---|---|
| 16 | 2-F-C6H4-CH(OH)-CH2-CH2-NH-S(O)2-NH2 | Not done | Not done | >300 μM | >300 μM | — |
| 17 | 2-Cl-C6H4-CH(OH)-CH2-CH2-NH-S(O)2-NH2 | Not done | Not done | >300 μM | >300 μM | — |
| 18 | 2-Cl-C6H4-CH(OH)-CH2-CH2-NH-S(O)2-NH2 | 100 nM | 1 μM | 1 nM | 1 nM | — |
| 19 | 4-(2-F-C6H4)-4-OH-piperidine-N-S(O)2-NH2 | 1.0 nM | 1 μM | 1 μM | 1 μM | 6 hrs at 100 mg/kg |
| 20 | 2-CF3-C6H4-CH(OH)-CH2-CH2-NH-S(O)2-NH2 | >300 μM | >300 μM | Not done | Not done | — |
| 21 | 2-NO2-C6H4-CH(OH)-CH2-CH2-NH-S(O)2-NH2 | 10 μM | >300 μM | Not done | Not done | — |
| 22 | 2,6-F2-C6H3-CH(OH)-CH2-CH2-NH-S(O)2-NH2 | 300 μM | 100 μM | 10 nM | 1 μM | — |
| 23 | 2-Ph-C6H4-CH(OH)-CH2-CH2-NH-S(O)2-NH2 | 300 μM | 10 μM | Not done | Not done | — |

TABLE 3-continued

Examples of Propyl Hydroxylated Sulfamide Compounds and their Potencies for Biological Activity

| Example number | Structures | NP* from Glutamate PI | NP* from Glutamate CFDA | NP** from HP PI | NP** from HP CFDA | MES*** Duration |
|---|---|---|---|---|---|---|
| | | | EC50 | | | |
| 24 | 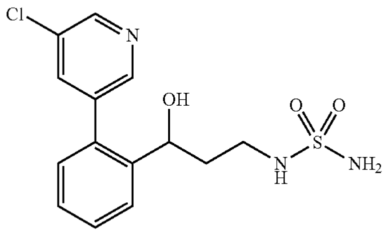 [SMILES: NS(=O)(=O)NCCC(O)c1ccccc1-c1cncc(Cl)c1] | >300 μM | 10 μM | Not done | Not done | — |

*NP = Neuroprotection from 30 μM glutamate in Hippocampal Cultures
**NP = Neuroprotection from 10 μM Hydrogen Peroxide in Hippocampal Cultures
***MES = Maximal Electroshock Test in mice (anti-seizure test)

What is claimed is:

1. A compound having formula (I):

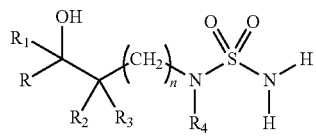

(I)

including hydrates, solvates, and pharmaceutically acceptable salts thereof, wherein:
R is selected from the group consisting of optionally substituted aryl, optionally substituted benzoisoxazole, and optionally substituted benzothiophene where R may be substituted by 0-5 moieties;
n is 1 or 2;
$R^1$ is selected from the group consisting of hydrogen and optionally substituted $C_{1-6}$ alkyl;
$R^2$, $R^3$, and $R^4$ are each independently selected from the group consisting of hydrogen, halogen, and optionally substituted $C_{1-6}$ alkyl; and
$R^1$ and $R^4$ are taken together with atoms to which they are bound to form an optionally substituted ring having from 5 to 7 ring atoms.

2. The compound according to claim 1 wherein R is 2-phenyl, 2-fluorophenyl, 3-fluorophenyl, 4-fluorophenyl, 2,4-difluorophenyl, 2,5-difluorophenyl, 2,6-difluorophenyl, 2-chlorophenyl, 2-bromophenyl, 2-trifluoromethylphenyl, 3-trifluoromethylphenyl, 2,6-dichlorophenyl, 2,4-dichlorophenyl, 2-methylphenyl, 2-ethylphenyl, 2-methoxyphenyl, 2-chloro-6-fluorophenyl, 2-chloro-4-fluorophenyl, 2-fluoro-6-methoxyphenyl, 4-fluoro-2-methoxyphenyl, 2-chloro-6-methoxyphenyl, benzo[b]thiophen-3-yl, or benzo[b]isoxazol-3-yl.

3. The compound according to claim 1 wherein $R_1$ is methyl or hydrogen.

4. The compound according to claim 1 wherein $R_2$ is methyl or hydrogen.

5. The compound according to claim 1 wherein $R_3$ is methyl or hydrogen.

6. The compound according to claim 1 wherein n is 1.

7. The compound according to claim 1, wherein n is 2.

8. The compound according to claim 1 wherein the optionally substituted ring containing $R_1$ and $R_4$ is a six-membered ring.

9. The compound according to claim 1 having formula II

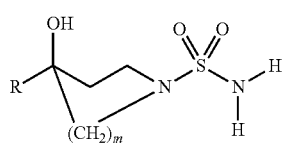

(II)

wherein R is selected from the group consisting of optionally substituted aryl, optionally substituted benzoisoxazole, and optionally substituted benzothiophene where R may be substituted by 0-5 moieties; and
m is 1, 2 or 3.

10. The compound according to claim 1 that is:
3-phenyl-3-hydroxypropyl-1-sulfamide;
3-(2-fluorophenyl)-3-hydroxypropyl-1-sulfamide;
3-(2-fluorophenyl)-3-methyl-3-hydroxypropyl-1-sulfamide;
3-(2-fluorophenyl)-3-hydroxy-2,2-dimethylpropyl-1-sulfamide;
4-(2-fluorophenyl)-4-hydroxybutyl-1-sulfamide;
3-(3-fluorophenyl)-3-hydroxypropyl-1-sulfamide;
3-(4-fluorophenyl)-3-hydroxypropyl-1-sulfamide;
3-(2,4-fluorophenyl)-3-hydroxypropyl-1-sulfamide;
3-(2,5-fluorophenyl)-3-hydroxypropyl-1-sulfamide;
3-(2,6-fluorophenyl)-3-hydroxypropyl-1-sulfamide;
3-(2-chlorophenyl)-3-hydroxypropyl-1-sulfamide;
3-(2-chlorophenyl)-3-methyl-3-hydroxypropyl-1-sulfamide;
4-(2-chlorophenyl)-4-hydroxybutyl-1-sulfamide;
3-(2-bromophenyl)-3-hydroxypropyl-1-sulfamide;
3-(2-trifluoromethylphenyl)-3-hydroxypropyl-1-sulfamide;
3-(3-trifluoromethylphenyl)-3-hydroxypropyl-1-sulfamide;
3-(2,6-dichlorophenyl)-3-hydroxypropyl-1-sulfamide;
3-(2,4-dichlorophenyl)-3-hydroxypropyl-1-sulfamide;
3-(2-methylphenyl)-3-hydroxypropyl-1-sulfamide;
3-(2-ethylphenyl)-3-hydroxypropyl-1-sulfamide;
3-(2-methoxyphenyl)-3-hydroxypropyl-1-sulfamide;

3-(2-chloro-4-fluorophenyl)-3-hydroxypropyl-1-sulfamide;
3-(2-chloro-6-fluorophenyl)-3-hydroxypropyl-1-sulfamide;
3-(2-fluoro-6-methoxyphenyl)-3-hydroxypropyl-1-sulfamide;
3-(4-fluoro-2-methoxyphenyl)-3-hydroxypropyl-1-sulfamide;
3-(2-chloro-6-methoxyphenyl)-3-hydroxypropyl-1-sulfamide;
3-(benzo[b]thiophen-3-yl)-3-hydroxypropyl-1-sulfamide;
3-(benzo[b]isoxazol-3-yl)-3-hydroxypropyl-1-sulfamide;
or a pharmaceutically acceptable salt thereof.

11. The compound according to claim 1 that is:
4-phenyl-4-hydroxypiperidine-1-sulfonamide;
3-(2-fluorophenyl)-3-hydroxypyrrolidine-1-sulfonamide;
4-(2-fluorophenyl)-4-hydroxypiperidine-1-sulfonamide;
4-(2-fluoro-phenyl)-4-hydroxyazepane-1-sulfonamide;
4-(4-fluorophenyl)-4-hydroxypiperidine-1-sulfonamide;
4-(2,6-difluorophenyl)-4-hydroxypiperidine-1-sulfonamide;
4-(2-chlorophenyl)-4-hydroxypiperidine-1-sulfonamide;
4-(2-chlorophenyl)-4-hydroxyazepane-1-sulfonamide;
4-(2-trifluoromethylphenyl)-4-hydroxypiperidine-1-sulfonamide;
4-(3-trifluoromethylphenyl)-4-hydroxypiperidine-1-sulfonamide;
4-(2-methylphenyl)-4-hydroxypiperidine-1-sulfonamide;
4-(2-methoxyphenyl)-4-hydroxypiperidine-1-sulfonamide;
4-(2-fluoro-6-methoxyphenyl)-4-hydroxypiperidine-1-sulfonamide;
4-benzo[b]thiophen-3-yl-4-hydroxypiperidine-1-sulfonamide;
4-benzo[b] isoxazol-3-yl-4-hydroxypiperidine-1-sulfonamide;
or a pharmaceutically acceptable salt thereof.

12. A composition comprising an effective amount of at least one compound according to claim 1.

13. A composition according to claim 12, further comprising at least one excipient.

14. A composition according to claim 13, wherein the at least one compound is at least one member selected from the group consisting of:
3-phenyl-3-hydroxypropyl-1-sulfamide;
3-(2-fluorophenyl)-3-hydroxypropyl-1-sulfamide;
3-(2-fluorophenyl)-3-methyl-3-hydroxypropyl-1-sulfamide;
3-(2-fluorophenyl)-3-hydroxy-2,2-dimethylpropyl-1-sulfamide;
4-(2-fluorophenyl)-4-hydroxybutyl-1-sulfamide;
3-(3-fluorophenyl)-3-hydroxypropyl-1-sulfamide;
3-(4-fluorophenyl)-3-hydroxypropyl-1-sulfamide;
3-(2,4-fluorophenyl)-3-hydroxypropyl-1-sulfamide;
3-(2,5-fluorophenyl)-3-hydroxypropyl-1-sulfamide;
3-(2,6-fluorophenyl)-3-hydroxypropyl-1-sulfamide;
3-(2-chlorophenyl)-3-hydroxypropyl-1-sulfamide;
3-(2-chlorophenyl)-3-methyl-3-hydroxypropyl-1-sulfamide;
4-(2-chlorophenyl)-4-hydroxybutyl-1-sulfamide;
3-(2-bromophenyl)-3-hydroxypropyl-1-sulfamide;
3-(2-trifluoromethylphenyl)-3-hydroxypropyl-1-sulfamide;
3-(3-trifluoromethylphenyl)-3-hydroxypropyl-1-sulfamide;
3-(2,6-dichlorophenyl)-3-hydroxypropyl-1-sulfamide;
3-(2,4-dichlorophenyl)-3-hydroxypropyl-1-sulfamide;
3-(2-methylphenyl)-3-hydroxypropyl-1-sulfamide;
3-(2-ethylphenyl)-3-hydroxypropyl-1-sulfamide;
3-(2-methoxyphenyl)-3-hydroxypropyl-1-sulfamide;
3-(2-chloro-4-fluorophenyl)-3-hydroxypropyl-1-sulfamide;
3-(2-chloro-6-fluorophenyl)-3-hydroxypropyl-1-sulfamide;
3-(2-fluoro-6-methoxyphenyl)-3-hydroxypropyl-1-sulfamide;
3-(4-fluoro-2-methoxyphenyl)-3-hydroxypropyl-1-sulfamide;
3-(2-chloro-6-methoxyphenyl)-3-hydroxypropyl-1-sulfamide;
3-(benzo[b]thiophen-3-yl)-3-hydroxypropyl-1-sulfamide;
3-(benzo[b]isoxazol-3-yl)-3-hydroxypropyl-1-sulfamide; and
pharmaceutically acceptable salts thereof.

15. A composition according to claim 13, wherein the at least one compound is at least one member selected from the group consisting of:
4-phenyl-4-hydroxypiperidine-1-sulfonamide;
3-(2-fluorophenyl)-3-hydroxypyrrolidine-1-sulfonamide;
4-(2-fluorophenyl)-4-hydroxypiperidine-1-sulfonamide;
4-(2-fluoro-phenyl)-4-hydroxyazepane-1-sulfonamide;
4-(4-fluorophenyl)-4-hydroxypiperidine-1-sulfonamide;
4-(2,6-difluorophenyl)-4-hydroxypiperidine-1-sulfonamide;
4-(2-chlorophenyl)-4-hydroxypiperidine-1-sulfonamide;
4-(2-chlorophenyl)-4-hydroxyazepane-1-sulfonamide;
4-(2-trifluoromethylphenyl)-4-hydroxypiperidine-1-sulfonamide;
4-(3-trifluoromethylphenyl)-4-hydroxypiperidine-1-sulfonamide;
4-(2-methylphenyl)-4-hydroxypiperidine-1-sulfonamide;
4-(2-methoxyphenyl)-4-hydroxypiperidine-1-sulfonamide;
4-(2-fluoro-6-methoxyphenyl)-4-hydroxypiperidine-1-sulfonamide;
4-benzo[b]thiophen-3-yl-4-hydroxypiperidine-1-sulfonamide;
4-benzo[b] isoxazol-3-yl-4-hydroxypiperidine-1-sulfonamide; and
pharmaceutically acceptable salts thereof.

* * * * *